(12) United States Patent
Craig et al.

(10) Patent No.: US 9,131,669 B2
(45) Date of Patent: Sep. 15, 2015

(54) ANTIBODY PRODUCTION

(71) Applicants: Roger Kingdon Craig, Cheshire (GB); Franklin Gerardus Grosveld, Rotterdam (NL); Richard Wilhelm Janssens, Rotterdam (NL); Marinus Johannes Van Haperen, Prinsenbeek (NL)

(72) Inventors: Roger Kingdon Craig, Cheshire (GB); Franklin Gerardus Grosveld, Rotterdam (NL); Richard Wilhelm Janssens, Rotterdam (NL); Marinus Johannes Van Haperen, Prinsenbeek (NL)

(73) Assignee: ERASMUS UNIVERSITY MEDICAL CENTER, Rotterdam (NL)

( * ) Notice: Subject to any disclaimer, the term of this patent is extended or adjusted under 35 U.S.C. 154(b) by 0 days.

(21) Appl. No.: 13/815,676

(22) Filed: Mar. 14, 2013

(65) Prior Publication Data

US 2013/0330771 A1 Dec. 12, 2013

Related U.S. Application Data

(63) Continuation of application No. 13/140,529, filed as application No. PCT/GB2009/002781 on Nov. 30, 2009.

(30) Foreign Application Priority Data

| Dec. 18, 2008 | (GB) | .................................... 0823147.4 |
| Apr. 17, 2009 | (GB) | .................................... 0906673.9 |
| May 28, 2009 | (GB) | .................................... 0909207.3 |
| May 28, 2009 | (GB) | .................................... 0909208.1 |

(51) Int. Cl.
*C12P 21/08* (2006.01)
*A01K 67/027* (2006.01)
*C07K 16/00* (2006.01)
*C12N 15/85* (2006.01)

(52) U.S. Cl.
CPC ......... *A01K 67/0276* (2013.01); *A01K 67/0278* (2013.01); *A01K 2217/072* (2013.01); *A01K 2217/15* (2013.01); *A01K 2217/206* (2013.01); *A01K 2227/105* (2013.01); *A01K 2267/01* (2013.01); *C07K 16/00* (2013.01); *C12N 15/8509* (2013.01)

(58) Field of Classification Search
USPC .......................................................... 800/6
See application file for complete search history.

(56) References Cited

U.S. PATENT DOCUMENTS

| 5,591,669 | A | 1/1997 | Krimpenfort et al. |
| 5,814,318 | A | 9/1998 | Lonberg et al. |
| 5,877,397 | A | 3/1999 | Lonberg et al. |
| 6,162,963 | A | 12/2000 | Kucherlapati et al. |
| 6,596,541 | B2 † | 7/2003 | Murphy |
| 8,502,018 | B2 † | 8/2013 | Murphy |
| 2003/0144484 | A1 | 7/2003 | Le et al. |
| 2006/0015949 | A1 | 1/2006 | Lonberg et al. |

FOREIGN PATENT DOCUMENTS

| EP | 1399559 B1 | 3/2004 |
| WO | WO/90/04036 A1 | 4/1990 |
| WO | WO/90/10077 A1 | 9/1990 |
| WO | WO/93/12227 A1 | 6/1993 |
| WO | WO/94/04667 A1 | 3/1994 |
| WO | WO/98/24893 A2 | 6/1998 |
| WO | WO03/000737 A2 | 1/2003 |
| WO | WO2006/008548 A2 | 1/2006 |
| WO | WO2006/047367 A2 | 5/2006 |
| WO | WO2007/096779 A2 | 8/2007 |
| WO | WO2008/035216 A2 | 3/2008 |
| WO | WO2008/151081 A1 | 12/2008 |
| WO | WO2009/013620 A2 | 1/2009 |
| WO | WO2010/109165 A2 | 9/2010 |

OTHER PUBLICATIONS

IGKV3-20 Gene.*
IGVK1-33 Gene.*
IGVK1-39 Gene.*
Brezinschek et al., J. Immunol., 1995, 155: 190-203.*
de Wildt et al., J. Mol. Biol., 1999, 285: 895-901.*
IGKV3-20 Gene, Apr. 8, 2014.*
IGVK1-33 Gene, Apr. 8, 2014.*
Bell, A.C. et al., "The Protein CTCF is Required for the Enhancer Blocking Activity of Vertebrate Insulators," Cell, vol. 98, pp. 387-396, 1999.
Boland, M.J. et al., "Adult mice generated from induced pluripotent stem cells," Nature, vol. 461, No. 7260, pp. 91-94, 2009.
Colbere-Garapin, F. et al., "A new dominant hybrid selective marker for higher eukaryotic cells," J. Mol. Biol., vol. 150, pp. 1-14, 1981.
Davis, J.M. et al., "A simple, single-step technique for selecting and cloning hybridomas for the production of monoclonal antibodies," J. Immunol. Methods, vol. 50, No. 2, pp. 161-171,1982.
De Franco, A.L. et al., "Signal transduction by the B-cell antigen receptor," Ann. NY Acad. Sci., vol. 766, pp. 195-201, 1995.
Degner, S.C. et al., "Cutting Edge: Developmental stage-specific recruitment of cohesin to CTCF sites throughout immunoglobulin loci during B lymphocyte development," J. Immunol., vol. 182, pp. 44-48, 2009.
Degner, S.C. et al., "CCCTC-binding factor (CTCF) and cohesin influence the genomic architecture of the Igh locus and antisense transcription in pro-B cells," PNAS, pp. 1-6, 2011.
Ebert, A., et al., "The Distal $V_H$ Gene Cluster of the Igh Locus Contains Distinct Regulatory Elements with Pax5 Transcription Factor-Dependent Activity in Pro-B Cells," Immunity, vol. 34, pp. 175-187, 2011.

(Continued)

*Primary Examiner* — Ileana Popa
(74) *Attorney, Agent, or Firm* — Saul Ewing LLP

(57) ABSTRACT

A transgenic non-human mammal containing a heterologous lambda light chain gene locus, and/or a heterologous kappa light chain gene locus, and/or a heterologous heavy chain gene locus, each of which can re-arrange so that immunoglobulin heavy and light chain genes are formed and expressed in B-cells following antigen challenge.

12 Claims, 22 Drawing Sheets

(56) References Cited

OTHER PUBLICATIONS

Figure 1A:
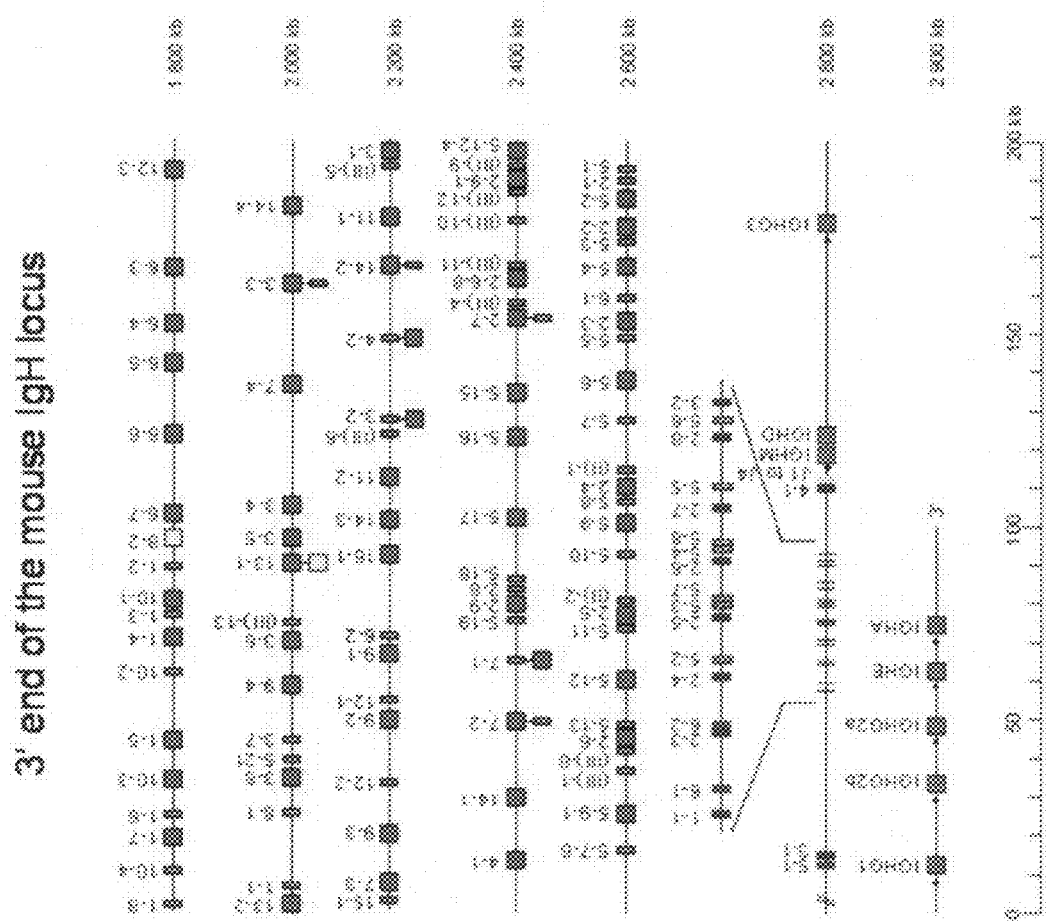

Festenstein, R. et al., "Locus Control Region Function and Heterochromatin-Induced Position Effect Variegation" Science, vol. 271, No. 5252, pp. 1123-1125, 1996.
Garrett, F.E. et al., "Chromatin Architecture near a Potential 3' End of the Igh Locus Involves Modular Regulation of Histone Modifications during B-Cell Development and in Vivo Occupancy at CTCF Sigtes," Mol. and Cellular Biol., vol. 25, No. 4, pp. 1511-1525, 2005.
Gottweis, H. et al., "iPS cells and the politics of promise," Nature Biotechnology, vol. 26, No. 3, pp. 271-272, 2008.
Guglielmi, L. et al., "Combination of 3' and 5' IgH regulatory elements mimics the B-specific endogenous expression pattern of IgH genes from pro-B to mature B cells in a transgenic mouse model," Biochim. Biophys. Acta, vol. 1642, pp. 181-190, 2003.
Guo, C., et al., "Two Forms of Loops Generate the Chromatin Conformation of the Immunoglobulin Heavy-Chain Gene Locus," Cell, vol. 147, pp. 332-343, 2011.
Guo, C., et al., "CTCF-binding elements mediate control of V(d)J recombination," Nature, vol. 477, pp. 424-430, 2011.
Hartman, S. et al., "Two dominant-acting selectable markers for gene transfer studies in mammalian cells," Proc. Natl. Acad. Sci. USA, vol. 85, No. 21, pp. 8047-8051, 1988.
Heinrich, G. et al., "Characterization of a human T cell specific chimeric antibody (CD7) with human constant and mouse variable regions," J. Immunol.,, vol. 143, pp. 3589-3597, 1989.
Janssens, R. et al., "Generation of heavy-chain-only antibodies in mice," PNAS, vol. 103, No. 41, pp. 15130-15135, 2006.
Jaton, J. et al., "Recovery of Antibody Activity upon Reoxidation of Completely Reduced Polyalanyl Heavy Chain and Its Fd Fragment Derived from Anti-2,4-dinitrophenyl Antibody," Biochemistry, vol. 7, No. 12, pp. 4185-4195, Dec. 1968.
Jhunjihunwala, S. et al., "The 3D structure of the immunoglobulin heavy-chain locus: implications for long-range genomic interactions," Cell, vol. 133, pp. 265-279, 2008.
Karreman, C., "New positive/negative selectable markers for mammalian cells on the basis of Blasticidin deaminase-thymidine kinase fusions," NAR, vol. 26, No. 10, pp. 2508-2510, 1998.
Kellermann, S. et al., "Antibody discovery: the use of transgenic mice to generate human monoclonal antibodies for therapeutics," Current Opinion in Biotechnology, vol. 13, pp. 593-597, 2002.
Kim, et al., "Analysis of the vertebrate insulator protein CTCF binding sites in the human genome," Cell, vol. 128, No. 6, pp. 1231-1245, 2007.
Kitamura, D. et al., "A B cell-deficient mouse by targeted disruption of the membrane exon of the immunoglobulin μ chain gene," Nature, vol. 350, pp. 423-426, 1991.
Li, et al., "Locus control regions: coming of age at a decade plus," Trends Genet., vol. 15, No. 10, pp. 403-408, 1999.
Lonberg, N. et al., "Antigen-specific Human Antibodies from Mice Comprising Four Distinct Genetic Modifications", Nature, vol. 368, No. 6474, pp. 856-859, 1994.
Lonberg, N., "Human antibodies from transgenic animals," Nature Biotechnology, vol. 23, No. 9, pp. 1117-1125, 2005.
Madisen, L. et al., "Identification of a locus control region in the immunoglobulin heavy-chain locus that deregulates c-myc expression in plasmacytoma and Burkitt's lymphoma cells," Genes & Development, vol. 8, pp. 2212-2226, 1994.
Mendez, M.J. et al., "Functional Transplant of Megabase Human Immunoglobulin Loci Recapitulates Human Antibody Response in Mice," Nature Genetics, vol. 15, No. 2, pp. 146-156, 1997.
Mills, F.C. et al., "Enhancer complexes located downstream of both human immunoglobulin C-alpha genes," J. Exp. Med., vol. 186, pp. 845-858, 1997.
Milot, E. et al., "Heterochromatin Effects on the Frequency and Duration of LCR-Mediated Gene Transcription," Cell, vol. 87, pp. 105-114, 1996.
Morrison, S.L. et al., "Chimeric human antibody molecules: Mouse antigen-binding domains with human constant region domains," Proc. Natl. Acad. Sci. USA, vol. 81, pp. 6851-6855, Nov. 1984.
Neuberger, M.S. et al., "A hapten-specific chimaeric IgE antibody with Human physiological effector function," Nature, vol. 314, pp. 268-270, 1985.
Neuberger, M.S. et al., "Construction of novel antibodies by use of DNA transfection: design of plasmid vectors," Phil. Trans. R. Soc. Lond., A317, pp. 425-432, 1986.
Nussenzweig, M.C. et al., "Allelic exclusion in transgenic mice that express the membrane form of immunoglobulin μ," Science, vol. 236, No. 4803, pp. 816-819, 1987.
Pettersson, S., et al., "Temporal Control of IgH Gene Expression in Developing B Cells by the 3'Locus Control Region," Immunobiol., vol. 198, pp. 236-248, 1997.
Ribeiro De Almeida, C. et al., Immunity, vol. 35, No. 4, pp. 501-513, 2011.
Riele, H.T. et al., "Highly efficient gene targeting in embryonic stem cells through homologous recombination with isogenic DNA constructs," Proc. Natl. Acad. Sci, USA, vol. 89, No. 11, pp. 5128-5132, 1992.
Santerre, R.F. et al., "Expression of Prokaryotic Genes for Hygromycin B and G418 Resistance as Dominant-Selection Markers in Mouse L Cells," Gene, vol. 30, pp. 147-156, 1984.
Singh, N. et al., "Biallelic germline transcription at the kappa immunoglobulin locus," J Exp. Med., vol. 197, pp. 743-750, 2003.
Slifka, M.K. et al., "Humoral immunity due to long-lived plasma cells," Immunity, vol. 8, No. 3, pp. 363-372, 1998.
Solter, D., "Dolly is a Clone-and No Longer Alone," Nature, vol. 394, pp. 315-316, 1998.
Splinter, E. et al., "CTCF mediates long-range chromatin looping and local histone modification in the β-globin locus," Genes Dev., vol. 20, No. 17, pp. 2349-2354, 2006.
Sun, L.K. et al., "Chimeric antibody with human constant regions and mouse variable regions directed against carcinoma-associated antigen 17-1A," Proc. Natl. Acad. Sci. USA, vol. 84, pp. 214-218, Jan. 1987.
Truffinet, V. et al., "The 3' IgH Locus Control Region is Sufficient to Deregulate a c-myc Transgene and Promote Mature B Cell Malignancies with a Predominant Burkitt-Like Phenotype," J. Immunol., vol. 179, pp. 6033-6042, 2007.
Tuaillon, N., "Repertoire analysis in human immunoglobulin heavy chain minilocus transgenic, muMT/muMT mice," Molecular Immunology, vol. 37, No. 5, pp. 221-231, 2000.
Vara, J.A. et al., "Expression in Mammalian Cells of a Gene from *Streptomyces alboniger* Conferring Puromycin Resistance," Nucleic Acids Research, vol. 14, pp. 4617-4624, 1986.
Wendt, K.S. et al., "Cohesin mediates transcriptional insulation by CCCTC-binding factor," Nature, vol. 451, No. 7180, pp. 796-801, 2008.
Xu, J.L. et al., "Diversity in the CDR3 Region of V(H) Is Sufficient for Most Antibody Specificities," Immunity, vol. 13, pp. 37-45, 2000.
Xu, L. et al., "Evidence that the Mouse 3' κ Light Chain Enhancer Confers Position-Independent Transgene Expression in T- and B-Lineage Cells," Human Gene Therapy, vol. 14, pp. 1753-1764, 2003.
Zou, Y-R. et al., "Cre-IoxP-mediated gene replacement: a mouse strain producing humanized antibodies," Current Biology, Current Science, GB, vol. 4, No. 12, pp. 1099-1103, 1994.
International Search Report based on International Application No. PCT/GB2009/002781, dated Apr. 19, 2010.
Co-pending U.S. Appl. No. 13/140,529, filed Sep. 6, 2011—IFW listing from PAIR only.
Translation of Search Report by Taiwanese Patent Office dated Jul. 30, 2014, regarding Taiwan Patent Application No. 098141093, filed on Dec. 1, 2009.
Xu, L. et al., "Evidence that the Mouse 3' κ Light Chain Enhancer Confers Position-Independent Transgene Expression in T- and B-Lineage Cells", Human Gene Therapy, vol. 14, p. 1753-1764 (2003).
Official Action by Japanese Patent Office dated Jun. 6, 2014, regarding Japanese Patent Application No. 2011-541578, filed on Nov. 30, 2009.
Bell, A. et al., "The Protein CTCF Is Required for the Enhancer Blocking Activity of Vertebrate Insulators," Cell, vol. 98, pp. 387-396 (1999).

(56) References Cited

OTHER PUBLICATIONS

Madisen, L. et al., "Identification of a locus control region in the immunoglobulin heavy-chain locus that deregulates c-myc expression in plasmacytoma and Burkitt's lymphoma cells," Genes Dev., Vol. 8, pp. 2212-2226 (1994).

Office Action dated Aug. 25, 2014 by Russian Patent Office, regarding Russian Patent Application No. 2011129459 filed on Nov. 30, 2009.

Glick et al., "Molecular Biotechnology. Principles and Applications of Recombinant DNA," 2nd Ed., ASM Press, Washington, DC, pp. 117 (1998).

Male et al., "Immunology," 7th Ed., Elsevier Ltd, pp. 81 (2006).

Pinaud, E. et al., "Localization of the 3' IgH Locus Elements that Effect Long-Distance Regulation of Class Switch Recombination," Immunity, vol. 15. pp. 187-199 (2001).

Office Action by Japanese Patent Office dated Feb. 27, 2015, regarding Japanese Patent Application No. 2011-541578, filed on Dec. 18, 2009.

Nicholson et al., "Antibody Repertoires of Four-and Five-Feature Translocus Mice Carrying Human Immunoglobulin Heavy Chain and K and X Light Chain Yeast Artificial Chromosomes," J. Immunol., vol. 163, pp. 6898-6906 (1999).

\* cited by examiner
† cited by third party

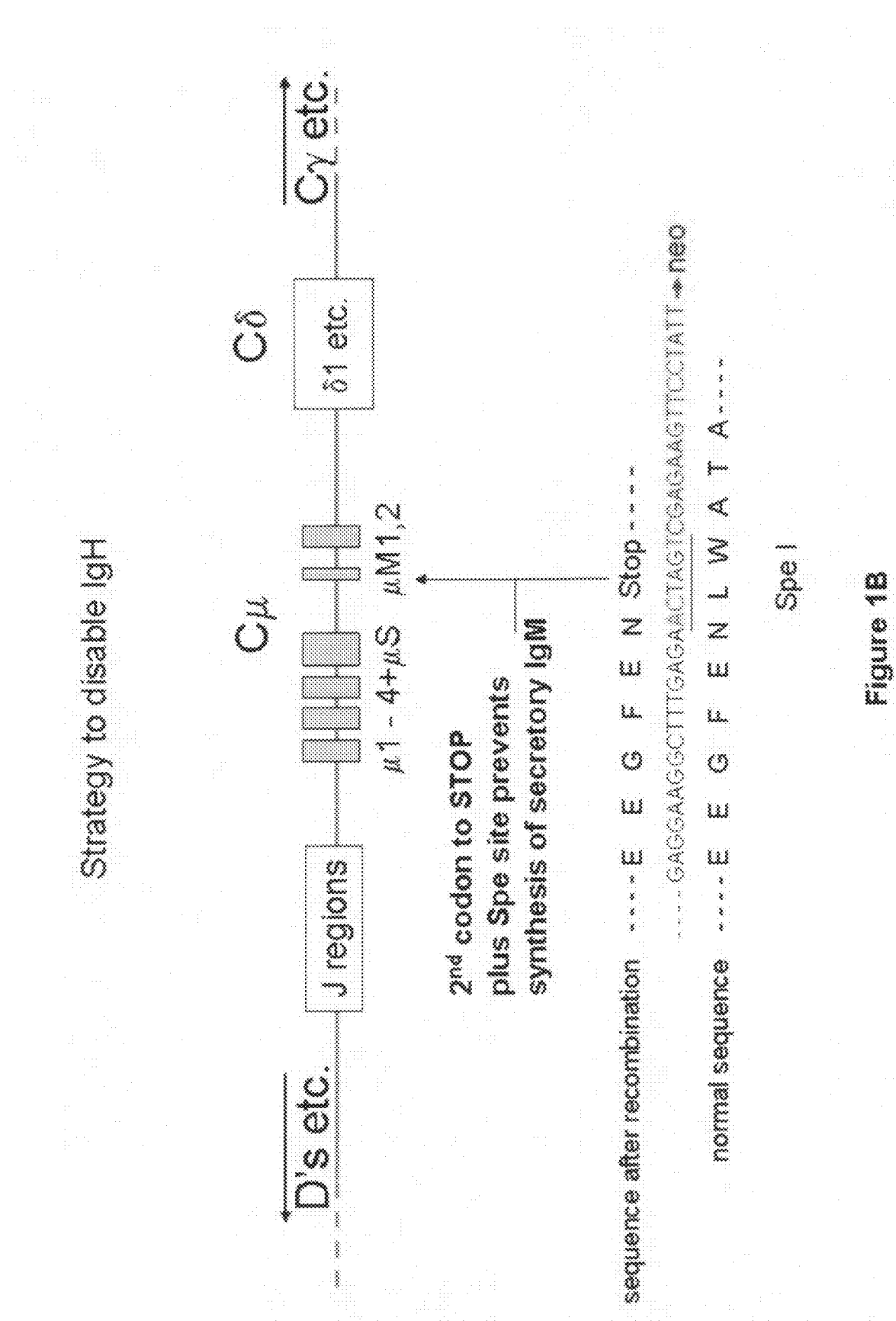

SEQUENCE LISTING

<160> NUMBER OF SEQ ID NOS: 13

<210> SEQ ID NO 1
<211> LENGTH: 6
<212> TYPE: PRT
<213> ORGANISM: Mouse

<400> SEQUENCE: 1

Glu Glu Gly Phe Glu Asn
1               5

<210> SEQ ID NO 2
<211> LENGTH: 37
<212> TYPE: DNA
<213> ORGANISM: Mouse

<400> SEQUENCE: 2
gaggaaggct ttgagaacta gtcgagaagt tcctatt                        37

<210> SEQ ID NO 3
<211> LENGTH: 11
<212> TYPE: PRT
<213> ORGANISM: Mouse

<400> SEQUENCE: 3

Glu Glu Gly Phe Glu Asn Leu Trp Ala Thr Ala
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Lox site insertion

<400> SEQUENCE: 4

Ile Thr Ser Tyr Cys Ile His Tyr Thr Leu Leu Cys
1               5                   10

<210> SEQ ID NO 5
<211> LENGTH: 60
<212> TYPE: DNA
<213> ORGANISM: Artificial Sequence
<220> FEATURE:
<223> OTHER INFORMATION: Lox site insertion

<400> SEQUENCE: 5
ggataacttc gtatagcata cattatacga agttatgctg atgctgcacc aactgtatcc    60

<210> SEQ ID NO 6
<211> LENGTH: 8
<212> TYPE: PRT
<213> ORGANISM: Mouse

<400> SEQUENCE: 6

Ala Asp Ala Ala Pro Thr Val Ser
1               5

<210> SEQ ID NO 7
<211> LENGTH: 26
<212> TYPE: DNA
<213> ORGANISM: Mouse

<400> SEQUENCE: 7
gggctgatgc tgcaccaact gtatcc                                    26

```
<210> SEQ ID NO 8
<211> LENGTH: 12
<212> TYPE: PRT
<213> ORGANISM: Artificial Sequence
<220> FEATURE:
<223> OTHER INFORMATION: Lox site insertion

<400> SEQUENCE: 8

Arg Ile Thr Ser Tyr Cys Ile His Tyr Thr Leu Leu
1               5                   10

<210> SEQ ID NO 9
<211> LENGTH: 72
<212> TYPE: DNA
<213> ORGANISM: Artificial Sequence
<220> FEATURE:
<223> OTHER INFORMATION: Lox site insertion

<400> SEQUENCE: 9
ggataacttc gtatagcata cattatacga agttatgatg auaauagagc tgatgctgca      60
ccaactgtat cc                                                         72

<210> SEQ ID NO 10
<211> LENGTH: 11
<212> TYPE: PRT
<213> ORGANISM: Artificial Sequence
<220> FEATURE:
<223> OTHER INFORMATION: Lox site insertion

<400> SEQUENCE: 10

Ile Thr Ser Tyr Ser Ile His Tyr Thr Lys Leu
1               5                   10

<210> SEQ ID NO 11
<211> LENGTH: 63
<212> TYPE: DNA
<213> ORGANISM: Artificial Sequence
<220> FEATURE:
<223> OTHER INFORMATION: Lox site insertion

<400> SEQUENCE: 11
gagcagttat gataatagat aacttcgtat agcatacatt atacgaagtt ataacatctg      60
gag                                                                   63

<210> SEQ ID NO 12
<211> LENGTH: 11
<212> TYPE: PRT
<213> ORGANISM: Mouse

<400> SEQUENCE: 12

Val Ser Ile Phe Pro Pro Ser Ser Glu Gln Leu
1               5                   10

<210> SEQ ID NO 13
<211> LENGTH: 35
<212> TYPE: DNA
<213> ORGANISM: Mouse

<400> SEQUENCE: 13
gtatccatct tcccaccatc cagtgagcag ttaac                                 35
```

ANTIBODY PRODUCTION

CROSS REFERENCE TO RELATED APPLICATIONS

The present application is continuation of application Ser. No. 13/140,529, which is a 35 U.S.C. 371 National Stage Application of International Application No. PCT/GB2009/002781, International filing Date: Nov. 30, 2009, which claims priority under 35 U.S.C. §119(a) to Great Britain Application No. 0823147.4, Filing Date: Dec. 18, 2008, and Great Britain Application No. 0906673.9, Filing Date: Apr. 17, 2009, and Great Britain Application No. 0909207.3, Filing Date: May 28, 2009, and Great Britain Application No. 0909208.1, Filing Date: May 28, 2009, each of which is incorporated herein by reference in its entirety.

FIELD OF THE INVENTION

The present invention relates to improved methods for the derivation and selection using transgenic non-human mammals of a diverse repertoire of functional, affinity-matured tetrameric immunoglobulins comprising heavy and light chains in response to antigen challenge and uses thereof.

In particular, the present invention relates to a non-human mammal, preferably a mouse, engineered such that either its ability to generate endogenous mouse kappa and/or lambda light chain immunoglobulins is substantially reduced, or the ability of light chains to complex with heavy chain is reduced, eliminated or blocked. The non-human mammals of the invention also have a reduced ability to generate functional endogenous mouse heavy chains. Thus, their ability to form functional immunoglobulin tetramers comprising re-arranged heavy and light chains produced from said mutated loci has been substantially reduced or eliminated. Methods of generating such mammals and methods of using such mammals to generate human tetrameric antibodies and hybrid tetrameric antibodies using immunoglobulin heavy and light chain transgenes are also described.

In the following description, all amino acid residue position numbers are given according to the numbering system devised by Kabat et al. (1991) US Public Health Services publication No 91-3242.

BACKGROUND TO THE INVENTION

Antibodies

The structure of antibodies is well known in the art. Most natural antibodies are tetrameric, comprising two heavy chains and two light chains. The heavy chains are joined to each other via disulphide bonds between hinge domains located approximately half way along each heavy chain. A light chain is associated with each heavy chain on the N-terminal side of the hinge domain. Each light chain is normally bound to its respective heavy chain by a disulphide bond close to the hinge domain.

When an antibody molecule is correctly folded, each chain folds into a number of distinct globular domains joined by more linear polypeptide sequences. For example, the light chain folds into a variable ($V_L$) and a constant ($C_\kappa$ or $C_\lambda$) domain. Heavy chains have a single variable domain $V_H$, a first constant domain ($C_H1$), a hinge domain and two or three further constant domains. The heavy chain constant domains and the hinge domain together form what is generally known as the constant region of an antibody heavy chain. Interaction of the heavy ($V_H$) and light ($V_L$) chain variable domains results in the formation of an antigen binding region (Fv). Interaction of the heavy and light chains is facilitated by the $C_H1$ domain of the heavy chain and the $C_\kappa$ or $C\lambda$ domain of the light chain. Generally, both $V_H$ and $V_L$ are required for antigen binding, although heavy chain dimers and amino-terminal fragments have been shown to retain activity in the absence of light chain (Jaton et al. (1968) Biochemistry, 7, 4185-4195). Generally the proportion of circulating λ light chain is low, representing perhaps 2-5% of the total light chain complexed as a tetrameric immunoglobulin in plasma (Goldsby et al. (2003) Immunology, 5th edition, W.H. Freeman & Co NY).

The in vitro manipulation of heavy chain immunoglobulin genes to construct novel antibodies was first described in the 1980s. Much of the early antibody engineering work used a rearranged mouse immunoglobulin µ gene (IgM) raised against a well-characterised antigen. A feature of this antibody was that antigen binding specificity was known to reside in the $V_H$ domains, since assembly and secretion with an irrelevant light chain showed retention of antigen binding (Neuberger and Williams (1986) Phil. Trans. R. Soc. Lond., A317, 425-432). Using this system, it was shown that a mouse antigen-specific $V_H$ binding domain could be used to derive a novel antibody comprising a human ε constant effector region fused to a mouse antigen-specific $V_H$ domain. The resulting hybrid IgE retained antigen specificity and showed effector activity expected of an IgE (Neuberger et al. (1985) Nature, 314, 268-270). Other literature examples of heavy chain engineering include: hybrid mouse-human antibody genes encoding mouse $V_H$ human/IgA or IgG antibody fusions which retain anti-phosphocholine activity (Morrison et al. (1984) PNAS, 81, 6851-6855); an anti-carcinoma-associated antigen 17-1A antibody comprising mouse $V_H$ and human IgG (γ3) constant region (Sun et al. (1987) PNAS, 84, 214-218); and an anti-human T-cell antibody (anti CD7) comprising human IgG (γ1) constant region and mouse $V_H$ domains (see Heinrich et al. (1989) J. Immunol., 143, 3589-97).

Normal human B cells contain a single immunoglobulin heavy chain locus on chromosome 14 from which the gene encoding a heavy chain is produced by rearrangement. In the mouse, the heavy chain locus is located on chromosome 12. A normal heavy chain locus comprises a plurality of V gene segments, a number of D gene segments and a number of J gene segments. Most of a $V_H$ domain is encoded by a V gene segment, but the C terminal end of each $V_H$ domain is encoded by a D gene segment and a J gene segment. VDJ rearrangement in B-cells, followed by affinity maturation, provides each $V_H$ domain with its antigen-binding specificity. Sequence analysis of normal $H_2L_2$ tetramers derived from a heavy chain immunoglobulin comprising a single V segment demonstrates that diversity in response to antigen challenge results primarily from a combination of VDJ rearrangement and somatic hypermutation (Xu and Davies (2000) Immunity, 13, 37-45). There are over 50 human V gene segments present in the human genome of which only 39 are functional. In normal diploid antibody-producing B-cells, each cell produces an antibody tetramer ($H_2L_2$) from a single set of heavy and light chain antibody loci. The other set of loci are not used productively as the result of a process called allelic exclusion (Singh et al. (2003) J. Exp. Med., 197, 743-750 and references therein).

Fully human antibodies ($H_2L_2$) can now be derived from transgenic mice in response to antigen challenge. Such transgenic mice generally comprise a single human heavy chain immunoglobulin locus and a separate human light chain immunoglobulin locus. The corresponding endogenous mouse heavy chain, kappa light chain and, optionally, lambda light chain loci coding sequences are deleted or partially deleted. Thus, only human antibodies comprising a kappa light chain are produced in a low background of mouse/human antibodies comprising a human heavy chain and a mouse lambda light chain (WO90/04036; WO93/12227; WO98/24893; US5877397, US5814318 and US6162963). The deletion of segments of all endogenous murine heavy and light chain immunoglobulin genes to eliminate endogenous heavy and light chain gene expression completely has been achieved but remains technically demanding, particularly if the elimination of all lambda light chain coding sequence is deemed necessary. Elimination of the murine lambda light chain coding sequence has been achieved through the complete deletion of all functional V and J gene segments and the C1, C2 and C3 constant regions of the lambda locus, resulting in a mouse with a silenced lambda light chain locus (see EP1399559).

A different approach is to limit mouse B-cell development and immunoglobulin secretion by disruption of membrane exons of the gene encoding the murine heavy chain gene. Thus, whilst the endogenous murine heavy chain gene is functional, in that it is transcribed and undergoes VDJ rearrangement in response to antigen challenge, since the IgM is never expressed on the cell surface of pre-B cells, further development is arrested, resulting in a non-productive response to antigen challenge (Kitamura et al. (1991) Nature, 350, 423-426), even though both endogenous mouse kappa and lambda light chain genes remain structurally intact and functional (Tuaillon (2000) Molecular Immunology, 37, 221-231).

Where endogenous mouse heavy chain and light chain gene loci remain functional, any additional introduced immunoglobulin heavy chain transgene is also regulated by allelic exclusion, so that some B-cells functionally express mouse heavy and light chain loci only and others human heavy chain loci only and mouse light chain loci (Nussenzweig et al. (1987) Science, 236, 816-819). In any single non-human transgenic animal, there is a highly diverse population of B-cells expressing antibodies derived from potentially all immunoglobulin loci in response to disparate antigen challenge. The subsequent selection of antigen-specific antibodies using established hybridoma technology using HAT selection (Davis et al. (1982) J. Immunol. Methods, 50, 161-171) does not distinguish between hybridomas expressing one as opposed to another heavy chain immunoglobulin locus.

Regulatory elements present in immunoglobulin heavy chain transgenes comprise essential tissue-specific enhancer elements to ensure B-cell specific expression in a copy number dependent manner. The presence of a 5' intronic enhancer and the 3' Locus Control Region ("LCR") ensures that transgenes are active at all stages of B-cell maturation (Guglielmi et al. (2003) Biochim. Biophys. Acta, 1642, 181-190). The inclusion of heavy and light chain specific LCRs in the transgene loci ensures not only that expression is B-cell specific, but that expression occurs irrespective of the site of integration into the genome (WO90/10077, Mills et al. (1997) J. Exp. Med., 186, 845-858 and Pettersson et al. (1997) Immunobiol., 198, 236-248)). Thus, provided an LCR is present, every transgene is functional irrespective of its position in the genome. In the event that the LCR present on the transgene is partially deleted, the chromatin surrounding the transgene is only partially open to transcription at any point in time, leading to positional effect mosaic expression, and so limited levels of expression of the transgene across the target tissue (Festenstein et al. (1996) Science, 23, 271 (5252):1123-5; Milot et al. (1996) Cell, 87(1), 105-14)

An alternative approach for the production of human immunoglobulins in a mouse background is to replace murine immunoglobulin gene segments with the homologous gene segments from humans. Thus, if only the mouse V, D and J gene segments are replaced by human homologues, a functional mouse/human hybrid antibody comprising human $V_H$ and $V_L$ domains and mouse constant (effector) regions will result following antigen challenge (WO94/04667). If all murine gene segments are replaced by human homologues, then an entirely human immunoglobulin will result following antigen challenge (US6596541). One perceived advantage of this approach is that, provided only coding regions are exchanged, then the resultant transgene retains all mouse regulatory elements, so ensuring maximal response to antigen challenge. This approach provides high serum titres of high affinity human antibodies or mouse/human hybrid antibodies depending on the final configuration of the transgenes. In reality, however, the replacement of all the individual V, D and J segments in the mouse genome by homologous recombination is a long and arduous task. Similarly, the construction of a heavy chain transgene comprising all 39 functional human V, D and J segments with constant (effector) regions is technically very demanding.

Therefore, there remains a need in the art for methods not dependent on the deletion of large segments of genomic DNA, or multiple deletions, which allow for (i) the simplified generation of mice either with a substantially reduced ability to express endogenous heavy and light chain immunoglobulin genes in a B-cell specific manner in response to antigen challenge, or which express endogenous immunoglobulin heavy and/or light chain genes in B-cells following antigen challenge but encode immunoglobulin heavy and light chain proteins which lack the ability to assemble as functional immunoglobulin tetramers, resulting in a non-productive response to antigen challenge; (ii) simplified and reproducible methods for the construction and B-cell-specific expression, of multiple heavy chain transgenic loci which may collectively comprise all 39 human V gene segments, but individually comprise preferred smaller groups of V gene segments, each in combination with all D and J gene segments and some or all constant (effector) regions, and whose functional expression is antigen dependent and ultimately determined by allelic exclusion; and (iii) the ability to select against hybridomas expressing residual endogenous mouse immunoglobulins and to select for hybridomas expressing and secreting assembled immunoglobulin tetramers comprising the full V segment repertoire present on the heavy chain transgenic loci, or alternatively to select for hybridomas which express a subset of V gene segments present on one as opposed to another heavy chain transgene locus.

THE INVENTION

According to a first aspect of the present invention, there is provided a non-human mammal containing an endogenous lambda light chain gene locus, an endogenous kappa light chain gene locus and an endogenous heavy chain gene locus, each of which can re-arrange so that immunoglobulin heavy and light chain genes are formed and expressed in B-cells following antigen challenge but said loci have been mutated so that the ability to form functional immunoglobulin tetramers comprising re-arranged heavy and light chains produced from said mutated loci has been substantially reduced or eliminated.

In the non-human mammal, at least one of the endogenous lambda light chain gene locus, the endogenous kappa light chain gene locus and the endogenous heavy chain gene locus may have been mutated by the introduction of a frame shift mutation, a polypeptide-encoding sequence and/or one or more stop codons into the or each endogenous locus.

The mutation is preferably an insertion of less than than 50 nucleotides.

In the non-human mammal, the expression of at least one of the endogenous lambda light chain gene locus, the endogenous kappa light chain gene locus and the endogenous heavy chain gene locus may have been substantially reduced by elimination of part or all of the LCR in the or each locus.

Preferably, the introduction is in the endogenous kappa light chain gene locus.

Alternatively, the introduction is in the endogenous lambda light chain gene locus.

In another alternative, the introduction is in the endogenous kappa light chain gene locus and the endogenous lambda light chain gene locus.

The introduction may also be in the endogenous heavy chain gene locus.

The introduction may in a further alternative be in the endogenous kappa light chain gene locus and in the endogenous heavy chain gene locus.

The introduction may in a yet further alternative be in the endogenous lambda light chain gene locus and in the endogenous heavy chain gene locus.

The introduction may in an even further alternative be in the endogenous lambda light chain gene locus, in the endogenous kappa light chain gene locus and in the endogenous heavy chain gene locus.

Preferably, there is an introduction, as defined in above, in the endogenous kappa light chain gene locus and there is a partial or complete LCR deletion, as defined above, in the endogenous lambda gene locus.

If desired, the endogenous heavy chain gene locus may be mutated such that heavy chain gene rearrangement, mRNA transcription and protein synthesis occurs but that B-cell activation is blocked.

Preferably, the non-human mammal as defined above comprises a transgene comprising one or more heterologous kappa light chain gene loci and associated B-cell specific regulatory elements.

The non-human mammal may further comprises a transgene comprising one or more heterologous lambda light chain gene loci and associated B-cell specific regulatory elements.

In the non-human mammal as defined above, the transgene may comprise a heterologous light chain gene locus comprises a dominant selective marker gene.

The non-human mammal as defined above may also comprise a transgene comprising one or more one or more heterologous heavy chain gene loci and associated B-cell specific regulatory elements.

If desired, the non-human mammal may comprise two or more transgenes comprising two or more different heterologous heavy chain gene loci and associated B-cell specific regulatory elements.

In the non-human mammal the or each transgene may comprise a heterologous heavy chain gene locus comprises a dominant selective marker gene.

In the non-human mammal, each heterologous heavy chain gene locus may comprise a CTCF binding sites.

Preferably, the non-human mammal comprises a transgene comprising a heterologous kappa light chain gene locus and a transgene comprising one or more heterologous heavy chain loci.

Alternatively, the non-human mammal may comprise a transgene comprising a heterologous lambda light chain gene locus and a transgene comprising one or more heterologous heavy chain loci.

In a further alternative, the non-human mammal may comprises a transgene comprising a heterologous kappa light chain gene locus, a transgene comprising a lambda light chain gene locus and a transgene comprising one or more heterologous heavy chain gene loci.

Preferably, each heterologous locus incorporates a cognate LCR.

Each heterologous locus is preferably a human locus.

However, each heterologous locus may be a hybrid locus comprising variable regions and constant regions derived from more than one species, such as a hybrid locus comprising human variable regions and rat or murine constant regions.

The non-human mammal may comprise groups of transgenes comprising different groups of different heterologous heavy chain gene loci, wherein each group of transgenes comprises a different dominant selective marker gene.

Alternatively, the non-human mammal may comprise transgenes comprising heterologous light chain loci and transgenes comprising heterologous heavy chain loci, wherein transgenes comprising heterologous light chain loci and transgenes comprising heterologous heavy chain loci each comprise a different dominant selective marker gene.

The non-human mammal is preferably a rodent, such as a mouse.

According to a second aspect, the present invention provides a method of producing an antigen-specific heterologous monoclonal antibody comprising:

(a) immunising a non-human transgenic mammal of any of the preceding claims with the antigen;

(b) preparing hybridomas or immortalised B-cell lines each of which produces a monoclonal antibody from the B-cells of the immunised transgenic mammal;

(c) optionally selecting at least one hybridoma or immortalised B-cell line expressing the heterologous antibody by use of the dominant selective marker genes present in the transgenes comprising the heterologous immunoglobulin light chain and heavy chain loci; and (d) selecting at least one hybridoma or immortalised B-cell line which produces an antibody which binds specifically to the antigen.

According to a further aspect of the present invention, there is provided a method of deriving a mammalian, preferably human, antibody from a hybrid antibody comprising:

(a) carrying out the method as described above;

(b) selecting at least one hybridoma or immortalised B-cell line which produces an antibody which binds specifically to the antigen and comprises $V_H$ and $V_L$ binding domains of the species of choice;

(c) cloning and sequencing the $V_H$ and $V_L$ domains;

(d) recloning selected sequences comprising the $V_H$ and $V_L$ binding domain coding sequences with constant effectors domains of choice from the same species; and (e) co-expressing the recloned sequences encoding heavy and light chain polypeptides of the desired species using an expression vector in a cell type of choice.

According to a yet further aspect of the invention, there is provided a method for the production of the non-human mammal as defined above comprising mutating the endogenous heavy chain gene locus, the endogenous kappa light chain gene locus, and optionally the endogenous lambda light chain gene locus in a mammalian progenitor cell and producing a mammal from said progenitor cell, wherein the mutation is such that, in the mammal, each locus can re-arrange so that immunoglobulin heavy and light chain genes are formed and expressed in B-cells following antigen challenge but the ability to form functional immunoglobulin tetramers comprising re-arranged heavy and light chains produced from said mutated loci has been substantially reduced or eliminated.

Preferably, the progenitor cell is a non-human embryonic stem cell.

The non-human mammal is preferably a rodent, such as a mouse.

The present invention also provides use of antigen-specific, heterologous, functional immunoglobulin tetramers, preferably human, derived using a non-human mammal or the method as defined above as medicaments, diagnostics or reagents.

The present inventors have surprisingly overcome the limitations of the prior art, through the development of simplified methods for the production of non-human mammals, particularly mice, wherein the functional expression of endogenous kappa and/or lambda light chain genes has been substantially reduced through either the constant regions being rendered non-functional as a result of a small insertional event preferably in the kappa constant region and/or lambda constant region, leading to a frame-shift or premature termination of mRNA translation, or elimination of part or all of the cognate endogenous LCR This contrasts with alternative strategies requiring the functional silencing of endogenous immunoglobulin light chain genes by complete or partial deletion of some or all light chain gene coding sequence.

The strategies described can be equally well applied to immunoglobulin heavy chain gene loci. Thus, for instance, complete or partial deletion of the LCR will result in a substantial reduction of heavy chain gene expression. The introduction of sequences leading to a frame-shift or premature termination of mRNA translation preferably in the $C_H1$ domain of the μC region, but alternatively in the $C_H1$ region of all immunoglobulin isotype constant regions, will substantially reduce, eliminate or block the formation of immunoglobulin tetramers with light chains. Similarly, as previously described, if IgM expression on the cell surface of pre-B cells is blocked in vivo by premature termination of mRNA translation, then further development is arrested, resulting in a non-productive response to antigen challenge (Kitamura et al. (1991) Nature, 350, 423-426). The introduction of a heavy chain immunoglobulin transgene rescues B-cell expansion and functional immunoglobulin tetramers comprising transgene-encoded heavy chain and endogenous murine light chains circulate in the plasma.

Thus, the ability of the endogenous light chain loci and/or heavy chain loci to produce heavy and light chains that interact and form functional immunoglobulin tetramers can be eliminated or substantially reduced following the introduction of a frame shift mutation, leading to the synthesis of irrelevent protein sequence, generally accompanied by premature termination of protein synthesis due to the presence of out-of-frame stop codons.

This can be achieved by the insertion of foreign DNA or a small deletion of DNA in or upstream of heavy or light chain polypeptide sequences responsible for the formation of functional immunoglobulin tetramers. The preferred approach is to insert new sequence. Effective insertional events designed either to cause a frame shift in the amino acid coding sequence, resulting in the premature termination of translation of the encoded mRNA, can be limited to the introduction of a single nucleotide. Thus, the insertion of one or more nucleocleotides within the coding region may lead to a frameshift. Alternatively the insertion of in-frame sequence encoding additional peptide sequences comprising a stop codon will also result in the synthesis of a truncated protein (U.S. Pat. No. 5,591,669). Targeted insertional events may also include the introduction of selective marker genes and other functionalities, provided that all the endogenous sequence is retained and the resulting fusion protein disrupts the formation of immunoglobulin tetramers, or the presence of one or more in-frame stop codon(s) leads to premature termination of mRNA translation, resulting in the synthesis of a truncated protein unable to form functional immunoglobulin tetramers.

Preferably, insertional events are in immunoglobulin κ light chain constant regions. Optionally, insertional events are in immunoglobulin κ and/or λ light chain constant regions. In practice, insertions may comprise any recombinase recognition site(s) such as a lox site. This alone may lead to a frame shift. The inclusion of additional nucleotides to ensure a frameshift, or codons for one or more stop codons, may also add to the effectiveness of the inserted sequence in the disruption of heavy and light chain dimerisation through the interaction of the heavy chain $C_H1$ domains and the light chain κ and/or λ constant regions. An insertion can comprise a single nucleotide, and is preferably less than 50 nucleotides. The insertion may result in only a frameshift, but preferably is designed such that one or more stop codons results in premature termination of mRNA translation. The insertion is performed using homologous recombination using arms which flank the site of insertion. Preferably, a selective marker is included during the manipulation process and then subsequently excised, leaving the recognition sites alone plus any additional inserted sequence in situ in the genome, e.g. lox sites.

It will be obvious to one skilled in the art that frame shifts and the synthesis of truncated proteins can also be achieved by the deletion of one or more nucleotides in the coding sequence and the inclusion of minimal additional sequence comprising stop codons. Preferably the insertion or deletion event occurs in the constant regions of the heavy and light chain genes and not in the multiple V, D and J regions of the endogenous loci. The preferred choice is the kappa light chain constant region.

Thus, there is no dependency on large scale gene deletion strategies for the elimination of endogenous immunoglobulin gene rearrangement or mRNA transcription. Identical insertional strategies can be used to inhibit the ability of endogenous heavy chain immunoglobulin to form functional tetrameric complexes with light chain through targeted insertional events within the $C_H1$ regions of heavy chain isotypes. Preferably, the expression of endogenous immunoglobulin heavy chain genes is blocked at the pre-B-cell stage such that the endogenous heavy chains are not expressed on the surface of B cells and productive expression resulting from B-cell expansion is blocked, using strategies similar to those described by Kitamura et al. (1991) Nature, 350, 423-426, whilst light chain association with the functional $C_H1$ of the endogenous IgM is inhibited by an insertional event leading to the translation of kappa and/or lambda light chain mRNA encoding light chain constant region(s) unable to functionally interact with the immunoglobulin heavy chain, preventing the formation of a functional endogenous immunoglobulin tetramer.

Provided the functional assembly of endogenous immunoglobulin tetramers is functionally impaired, B-cell expansion with associated affinity maturation of $V_H$ domains will be limited to and be dependent on the presence and expression of exogenous immunoglobulin heavy and light chain transgenes. The immunoglobulin transgenes will participate in the allelic exclusion process of the chosen non-human mammalian host in a B-cell specific manner, resulting in a productive response to antigen challenge, B-cell expansion and circulating, transgene-encoded antigen-specific immunoglobulin tetramers.

There is also provided a non-human mammal in which endogenous lambda light chain gene expression is substantially reduced by elimination of part or all of the lambda light chain LCR and endogenous kappa light chain gene expression is substantially reduced by elimination of part or all of the kappa light chain LCR. In one embodiment of the invention, only endogenous kappa light chain expression, or only lambda light chain expression, is substantially reduced by elimination of part or all of the relevant LCR.

The endogenous light chain loci may retain functionality in that they can rearrange and be transcribed into functional mRNA, but that the levels of transcription are substantially reduced through the elimination of some or all of the endogenous LCR functionality (WO90/10077). LCR functionality is removed by gene targeting nuclease hypersensitive sites in mouse ES cells or, in the absence of ES cells, by cloning using either nuclear transfer (Soulter (1998) Nature, 394, 315-316) or iPS cells (see Gottweiss, and Minger (2008) Nature Biotechnology, 26, 271-272) derived from other mammalian species. Alternatively, disruption of the heavy or light chains could be achieved through targeted mutagenesis, such as zinc finger nuclease technology and DNA repair (e.g, URL (without the lead http://www.)—sigmaaldrich.com/life-science/functional-genomics-and-rnai/zinc-finger-nuclease-technology).

Endogenous kappa light chain gene expression may be substantially reduced by elimination of part or all of the kappa light chain LCR, and the lambda light chain gene may be functionally silenced following deletion or insertional events.

Endogenous lambda light chain gene expression may be substantially reduced by elimination of part or all of the lambda light chain LCR, and the kappa light chain gene may be functionally silenced following deletion or insertional events.

Endogenous kappa light chain gene may be functionally silenced following LCR elimination or insertional events.

The invention also provides non-human mammals in which either or both endogenous kappa light chain gene expression and endogenous lambda light chain gene expression are substantially reduced by elimination of part or all of the kappa light chain LCR and/or elimination of part or all of the lambda light chain LCR. The endogenous kappa gene may be functionally silenced and endogenous lambda gene activity substantially reduced by elimination of part or all of the lambda light chain LCR.

Kappa light chain gene expression may be substantially reduced by elimination of part or all of the kappa light chain LCR reduced and lambda gene expression functionally silenced.

Only endogenous kappa light chain gene expression may be substantially reduced by elimination of the kappa chain LCR or functionally silenced by deletion or insertional events.

The non-human mammals having functionally silenced endogenous kappa and/or lambda light chain gene expression or substantially reduced endogenous kappa and/or lambda light chain gene expression as described above may also have reduced or functionally silenced endogenous heavy chain gene expression. According to one embodiment, endogenous heavy chain gene expression is reduced following the deletion of some or all nuclease hypersensitive sites which comprise the LCR or functionally silenced following deletion or insertional events in the non-human mammals of the invention. Preferably, the expression of endogenous heavy chain genes is blocked at the pre-B-cell stage such that the endogenous heavy chains are not expressed on the surface of B cells and productive expression resulting from B-cell expansion is blocked using strategies similar to those described by Kitamura et al. (1991) Nature, 350, 423-426.

The non-human mammals described above may further comprise one or more transgenes comprising heterologous heavy and light chain loci and associated B-cell specific regulatory elements, preferably comprising cognate LCRs.

In the context of the present invention, the term 'heterologous' means a nucleotide sequence or a locus as herein described which is not endogenous to the mammal in which it is located.

The non-human mammal may thus comprise a transgene comprising a heterologous kappa light chain locus and associated B-cell specific regulatory elements, preferably comprising an LCR and/or a transgene comprising a heterologous lambda light chain locus and associated B-cell specific regulatory elements, preferably comprising an LCR.

The presence of cognate LCRs is not essential for B-cell specific expression. Their inclusion within loci ensures that high level transgene expression occurs at every site of integration and is not dependent on random integration events, only some of which fortuitously occur within chromatin regions actively transcribed in B-cells. The use of cognate LCRs significantly reduces the number of transgenic animals required to be screened for antibody expression and allows the insertion of more than one gene locus, with the certainty that all loci inserted will be expressed at essentially normal levels in a B-cell specific manner. Thus, the use of LCR technology, combined with the surprising observation that allelic exclusion mechanisms will discriminate between endogenous immunoglobulin genes and multiple competing transgenes, opens the way for the assembly of transgenic non-human mammals comprising one or more immunoglobulin heavy or light chain gene loci, each locus being of reduced V gene complexity relative to the endogenous genes and comprising a relatively manageable piece of DNA (<300 Kb) to assemble in vitro relative to the endogenous loci (1-2 Mb). For example, the 39 functional human immunoglobulin heavy chain V gene segments may be cloned into two or more immunoglobulin heavy chain loci. Each will comprise different V gene segments, but have in common D and J gene segments, and constant (effector) regions. The inclusion of the LCR ensures that each is expressed in an identical manner, irrespective of the site of integration within the genome. Thus, the inclusion of two or more small loci in this manner provides the same V gene complexity of a single, more complex gene present in a single, large gene fragment which is technically difficult to manipulate.

Each heterologous light chain locus may comprise $V_L$ gene segments, J gene segments and a light chain constant region segment. Preferably, the $V_L$ and J gene segments and light chain constant region segment are derived from the same mammalian source, for example rodent, pig, cow, goat or sheep. Preferably, they are of human origin.

Alternatively, the heterologous light chain loci may be hybrid loci comprising variable domains of mammalian origin, preferably of human origin, and constant (effector) regions from a different mammal, such as, but not limited to, mouse, rat, hamster, rabbit, pig, goat and cow. Where the host mammal is a mouse, preferably the constant regions are of rodent origin, more preferably mouse or rat. Such heterologous light chain loci comprise $V_L$ and J segments preferably from one species only and a light chain constant region from another species.

Where hybrid kappa light chain transgenes are contemplated, the $V_L$ and J gene segments are preferably from the same species, contributing the heavy chain V, D and J gene segments, and are preferably of human origin. The kappa light chain constant and heavy chain constant regions are also preferably derived from the same species but a species different from that contributing variable domains and are preferably of rodent origin, and preferably derived from rat or mouse.

A feature of all light chain transgenes contemplated is that, following antigen challenge, the light chain rearranges in a B-cell specific manner and that, following transcription and translation, the resulting light chain is capable of complexing with transgene-derived heavy chain immunoglobulin produced in the same B-cell. The productive expression of immunoglobulin tetramers gives rise to B-cell expansion and transgene-encoded, antigen-specific tetravalent immunoglobulin complexes accumulate in serum in the absence of significant levels of endogenous immunoglobulin tetramers.

Where endogenous lambda light chain expression has not been functionally suppressed, then low levels of host or hybrid antibody comprising endogenous lambda light chains will be detectable. These may be discarded following screening of hybridoma supernatants.

In humans, there are 36 functional kappa $V_L$ gene segments, five $J_L$ gene segments and a single kappa light chain constant region (URL (without the lead http://)—imgt-.cines.fr). Preferably, a heterologous kappa light chain locus present in a transgene in the non-human mammal of the invention comprises one or more human $V_L$ gene segments, all human $J_L$ gene segments and a single human kappa light chain constant region. Optionally, the human kappa light chain constant region may be replaced by an alternate mammalian kappa light chain constant region, preferably of rat or mouse origin.

A heterologous lambda light chain locus present in a transgene in the non-human mammal of the invention preferably comprises a murine lambda LCR, and human lambda light chain V1 and V2 gene segments, human lambda J1, J2, J3 and J4 gene segments, and human lambda light chain C1, C2, C3 and C4 constant region segments (WO90/10077 and WO2003/000737). Optionally, the human lambda light chain C1, C2, C3 and C4 constant region segments may be replaced by alternative lambda light chain constant regions, preferably of rat or mouse origin.

A heterologous heavy chain locus present in a transgene in the non-human mammal of the invention preferably comprises a heavy chain immunoglobulin LCR, preferably of murine origin, one or more human V gene segments, one or more J gene segments and one or more D gene segments. Preferably, 10 or more human different V gene segments and all human J and D gene segments are present.

The locus also may comprise one or more human constant (effector) regions, preferably the μ and γ constant regions. Optionally, the human constant effector regions may be replaced by effector regions from other non-human mammals. Where the non-human mammalian host is a mouse or a rat, then preferably constant (effector) regions are derived from rat or mouse. In contrast with human, the transmembrane domains of the mouse and rat B-cell receptor complex (BCR) are 100% conserved. Thus, mice transgenic for antibody loci comprising rat constant (effector) region genes should function as well as those comprising mouse constant (effector) region genes following antigen challenge, and may be superior to those comprising human constant (effector) region genes (De Franco et al. (1995) Ann. NY Acad. Sci., 766, 195-201). The transgenes may comprise heavy chain, kappa and lambda light chain LCRs, preferably of mouse or human origin. LCRs which function across all mammalian species are known and may be substituted for human or mouse LCRs in the transgenes (Li et al. (1999) Trends Genet., 10, 403-8).

Where the generation of fully human antibodies is contemplated, cloned human antigen-specific $V_H$ and $V_L$ binding domains derived from hybrid antibodies expressed by hybridomas can be fused to human constant heavy and light chain constant regions, so deriving fully human tetrameric antibodies of any class.

As a further refinement, each immunoglobulin kappa and/or lambda light chain locus may also comprise a dominant selective marker gene.

The dominant selective marker genes incorporated in the loci may have the same or different mechanisms of action. For the purposes of the invention, any dominant selective marker gene can be used, provided that expression of the gene confers a selective benefit to hybridomas or transformed B-cells derived from the non-human transgenic mammal in the presence of a selective or toxic challenge. Typically, the dominant selective marker genes will be of prokaryotic origin and will be selected from a group which either confer resistance to toxic drugs, such as puromycin (Vara et al. (1986) NAR, 14, 4617-4624), hygromycin (Santerre et al. (1984) Gene, 30, 147-156) and G418 (Colbere-Garapin et al. (1981) 150, 1-14), or comprise genes which obviate certain nutritional requirements such that their expression converts a toxic substance into an essential amino acid, for example the conversion of indole to tryptophan or the conversion of histidinol to histidine (Hartmann and Mulligan, (1988) PNAS, 85, 8047-8051).

A necessary requirement of this aspect of the invention is that the dominant selective marker is incorporated within the immunoglobulin light chain transgenic locus and is co-expressed with the desired immunoglobulin light chain allele, so ensuring B-cell specific expression. Alternatively, the drug resistance gene may be inserted into an endogenous or exogenous (transgenic) immunoglobulin locus using homologous recombination in combination with ES cells or nuclear transfer approaches (te Riele et al. (1992), PNAS, 89, 11, 5128-5132).

The non-human mammal may also comprise a transgene or transgenes comprising a heterologous heavy chain locus and associated B-cell specific LCR and regulatory elements. More than one different transgenic heavy chain gene locus may be present, each comprising an LCR and regulatory elements.

The heavy chain gene loci, each comprising one or more V gene segments, one or more D gene segments, one or more J gene segments, and one or more constant (effector) regions are introduced as transgenes, each locus comprising a cognate LCR.

Each locus comprises the 5' and 3' regulatory elements necessary to drive B-cell specific expression. Each heavy or light chain locus is expressed in an essentially identical manner to the endogenous loci in response to antigen challenge, leading to the circulation in mouse serum of transgene-encoded, antigen-specific affinity-matured, tetrameric immunoglobulins.

Preferably, each heavy chain gene locus comprises one or multiple V gene segments, e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 60 or more V gene segments, which may be derived from any vertebrate species, preferably a non-human mammal. Preferably, not more than 20 V gene segments are present on any single heavy chain locus.

In one embodiment, each locus may comprise only one V gene segment. In one alternative of this embodiment, a number of V gene segments are present and each V gene segment is different from all other V gene segments. In this embodiment, the V gene segments in any one locus may all be derived from an organism of the same species, e.g. all V gene segments may be of human origin. Alternatively, the V gene segments in any one locus may be derived from organisms of different species, e.g. some V gene segments from human and others from sheep, cattle, rabbits, camelids or even shark. In a second alternative, each V gene segment is identical to all the other V gene segments. Irrespective of the number and nature of the V gene segments present, the remaining D and J gene segments in each locus may be the same as or may be different from those in all the other loci.

It is thus envisaged that the non-human mammal may contain multiple copies of a heavy chain gene locus. This has the advantage of optimising the chances that a productive re-arrangement in a B-cell will take place, thus allowing the optimal production of an immunoglobulin heavy chain for antigen recognition.

In another embodiment, each locus comprises multiple V gene segments.

Preferably, the V gene segments are of human origin.

The term 'V gene segment' encompasses any naturally occurring V gene segment derived from a vertebrate, including, but not limited to, sharks, rodents, camelids and human. The V gene segment must be capable of recombining with a D gene segment, a J gene segment and a gene segment encoding a heavy chain constant (effector) region to generate an immunoglobulin heavy chain antibody capable of complexing with either a kappa or lamdba immunoglobulin light chain when the re-arranged nucleic acid is expressed in B-cells.

A V gene segment also includes within its scope any gene sequence encoding a natural or engineered homologue, derivative or protein fragment which is capable of recombining with a D gene segment, a J gene segment and a gene segment encoding a heavy chain constant region to generate an immunoglobulin heavy chain antibody capable of complexing with either a kappa or lambda immunoglobulin light chain when the re-arranged nucleic acid is expressed in B-cells. A V gene segment may, for example, be derived from a T-cell receptor locus.

Preferably, the multiple heavy chain loci of the invention comprise any number or combination of the 39 functional human V gene segments and engineered variants thereof. These may be on any number of loci, e.g. four loci comprising eight V gene segments plus one locus comprising seven V gene segments; seven loci comprising four V gene segments plus one locus comprising three V gene segments; or thirty-nine loci comprising one V gene segment each.

Human V genes are classified into seven families, $V_H1$ to $V_H7$, and the individual genes within each family numbered. The frequency at which each gene is used is dependent on the varying requirements of the particular immune response. For example, the genes of family $V_H3$ may be preferentially used in comparison to those of family $V_H5$ when responding to bacterial antigens. Therefore, in a further preferred embodiment of the invention, groups of V gene segments which have been shown to be useful for generating an antibody response against specific antigens are grouped into separate loci, each comprising a different dominant selective marker gene. The V gene segments may be grouped according to family or they may be grouped according to individual function. For example, if the V genes of family $V_H3$ are shown to be useful for generating an immune response against bacterial antigens, then these may be used to generate a locus which is particularly useful for generating heavy chain-only antibodies against bacterial antigens. Alternatively, if it is shown that several individual genes from families $V_H3$ and $V_H5$ are useful for generating an immune response against bacterial antigens, then these may be grouped together and used to generate a locus which is particularly useful for generating antibodies against bacterial antigens.

An "immunoglobulin heavy chain locus" in the context of the present invention relates to a minimal micro-locus encoding a $V_H$ domain comprising one or more V gene segments, one or more D gene segments and one or more J gene segments, operationally linked to one or more gene segments encoding heavy chain constant (effector) regions. Preferably, the primary source of antibody repertoire variability is the CDR3 region formed by the selection of V, D and J gene segments and by the V-D and D-J junctions.

The advantage of the present invention is that antibody repertoire and diversity obtained in the rearranged V, D and J gene segments can be maximised through the use of multiple immunoglobulin heavy chain gene loci in the same transgenic non-human mammal by exploiting allelic exclusion. The process of allelic exclusion, which randomly chooses one of the loci to start recombination, followed by the next locus if the first recombination was non-productive, etc., until a productive recombination has been produced from one of the loci, would ensure that actually all the V gene segments present in the combined loci would be part of the overall recombination process.

To enhance the probability of all $V_H$ gene segments in any given immunoglobulin heavy chain locus participating productively in VDJ rearrangements, CTCF sites may be interdispersed between groups of VH gene segments.

The immunoglobulin locus in its normal configuration appears to have a three dimensional folded structure based on distance measurements made in B cells and measuring in the direction of and through the VH region (Jhunjhunwala et al. (2008) Cell, 133, 265-279). Such a folded or looped structure explains why different $V_H$ region can be used equally efficiently even when they are arranged at very different distances from the D, J and constant region of the immunoglobulin heavy chain locus.

It has also recently become clear that a folded structure formed by looping in a number of loci is mediated through a particular chromatin binding protein called CTCF. CTCF appears to be directly involved in the formation of chromatin looping as demonstrated by mutagenesis experiments (Splinter et al. (2006) Genes Dev., 20, 2349-2354). More recently it has been shown that cohesin, the protein complex that holds sister chromatids together, is present at CTCF binding sites (Wendt et al. (2008) Nature, 451, 796-801). The inclusion of a number of CTCF sites from the immunoglobulin $V_H$ region (Kim et al. (2007) Cell, 128, 1231-1245; Denger, Wong, Jankevicius and Feeney (2009) J. Immunol., 182, 44-48) increases the probability that the $V_H$ region of a transgenic immunoglobulin heavy chain locus can be folded properly and allow efficient usage of all the different V gene segments present in that locus.

Each transgene comprising a heterologous heavy chain locus may further comprise a dominant selective marker. Preferably, the dominant selective marker is different from the dominant selective marker introduced within the kappa or lambda light chain loci.

For the purpose of the invention, any dominant selective marker gene can be used, provided that expression of the gene confers a selective benefit to hybridomas or transformed B-cells derived from the non-human transgenic mammal in the presence of a selective or toxic challenge. Typically, the dominant selective marker genes will be of prokaryotic origin and will be selected from a group which either confer resistance to toxic drugs, such as puromycin (Vara et al. (1986) NAR, 14, 4617-4624), hygromycin (Santerre et al. (1984) Gene, 30, 147-156) and G418 (Colbere-Garapin et al. (1981) 150, 1-14), or comprise genes which obviate certain nutritional requirements such that their expression converts a toxic substance into an essential amino acid, for example the conversion of indole to tryptophan or the conversion of histidinol to histidine (see Hartmann and Mulligan (1988) PNAS, 85, 8047-8051).

A necessary requirement of the invention is that the dominant selective marker(s), if used, reside within the immunoglobulin heavy chain transgenic loci, so ensuring B-cell specific co-expression. Alternatively, the drug resistance gene may be inserted into an endogenous or exogenous (transgenic) immunoglobulin locus using homologous recombination in combination with ES cells or nuclear transfer approaches (e.g. to Riele, Robanus Maandag and Berns (1992), PNAS, 89, 11, 5128-5132).

The same dominant selective marker gene may be incorporated within all heavy chain loci. Alternatively, different heavy chain loci or groups of heavy chain loci may comprise different dominant selective marker genes.

Hybridomas or transformed B-cells, preferably transformed long-lived plasma cells (Slifka et al (1998) Immunity, 8, 363-372), derived from transgenic mice of the invention expressing tetrameric antibodies may be selected for, free of cells expressing endogenous immunoglobulin, due to the co-expression of a functional dominant selective marker gene within the transgenic light chain loci. Furthermore, hybridomas or transformed B-cell lines expressing antibodies derived from specific groups of V segments present on transgenic heavy chain loci may also be selected for due to the presence and co-expression of different dominant selective markers within heavy chain loci relative to the dominant selective markers incorporated within the light chain loci. For example, the inclusion of a puromycin resistance gene within the kappa light chain transgenic locus would allow selection of all cells expressing the kappa light chain transgene. Alternatively, the inclusion of the G418 resistance gene within a heavy chain transgenic locus comprising preferred V gene segments would allow the selection of all cells expressing the preferred V gene segments.

In particular, the invention provides a method of producing an antigen-specific heterologous monoclonal antibody comprising:
(a) immunising a non-human transgenic mammal as described above with the antigen;
(b) preparing hybridomas or immortalised B-cell lines each of which produces a monoclonal antibody from the B-cells of the immunised transgenic mammal;
(c) selecting at least one hybridoma or immortalised B-cell line expressing the heterologous antibody by use of the dominant selective marker genes present in the transgenes comprising the heterologous immunoglobulin light chain and heavy chain loci; and
(d) selecting at least one hybridoma or immortalised B-cell line which produces an antibody which binds specifically to the antigen.

The invention is now described, by way of example only, in the following detailed description with reference to the following Figures.

FIGURES

FIG. 1A: The 3' End of the Mouse IgH Locus.
The map is copied from the IMGT database (URL without the lead http reference) imgt.cines.f. The scale is in kilobases (kb). Green squares, functional $V_H$ segments; red and yellow squares, non-functional $V_H$ segments; orange squares, $J_H$ segments; blue squares, constant regions. The intronic IgH enhancer and the LCR at the 3' end of the locus are not indicated.

FIG. 1B: Strategy to Disable IgH
The top line shows the Cμ region of the mouse with the different exons including the two exons coding for the membrane form of IgM. To the left are the J, D and $V_H$ region of the locus, to the right the other constant regions starting with Cδ. The bottom lines show part of the amino acid sequence of the normal M1 exon after recombination. The DNA sequence shows the integration sequence. The stop codon is in red, the Spe I site in red and blue.

Figure 1C:
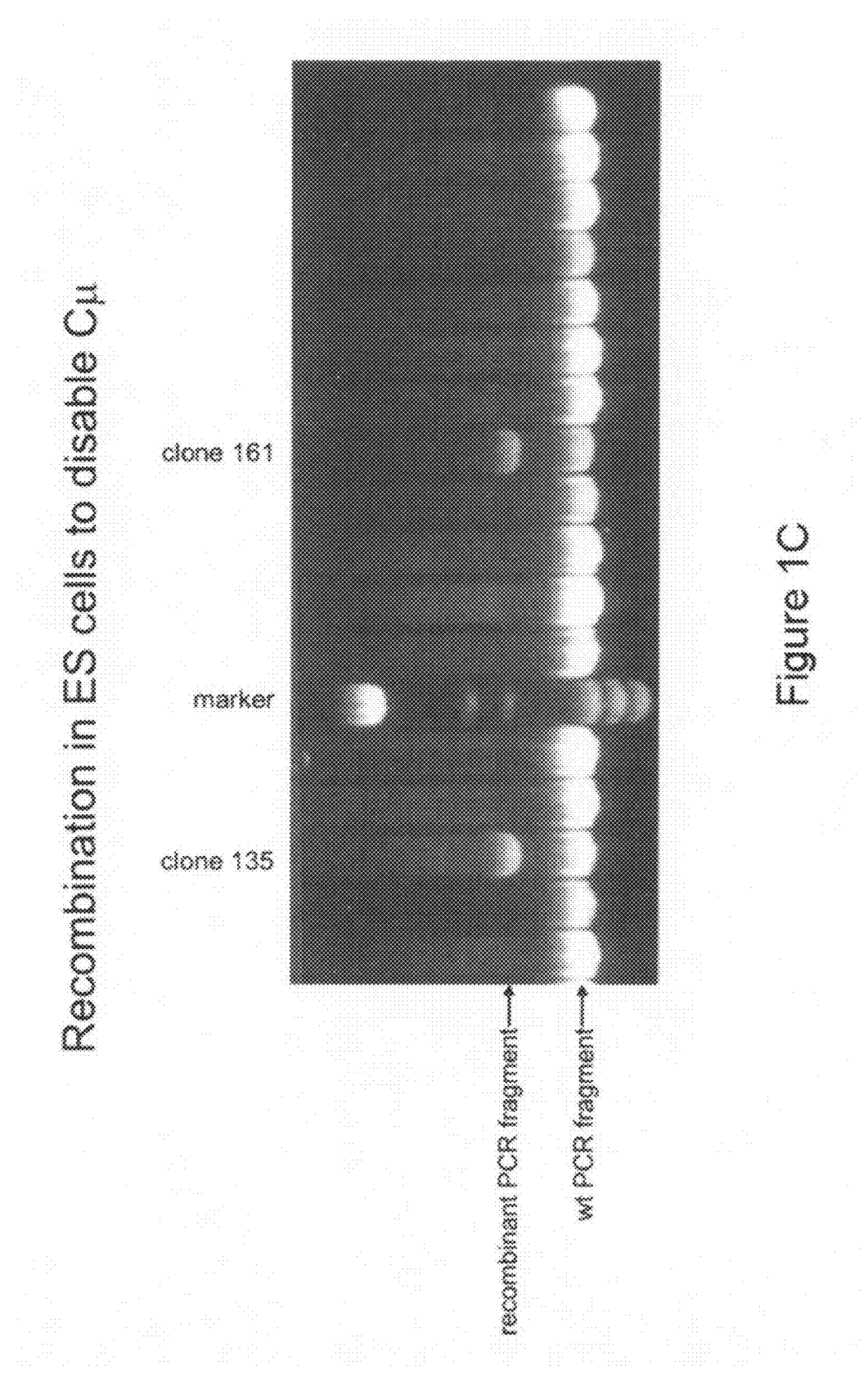

FIG. 1C: Recombination in ES Cells to Disable Cμ
This figure shows two of the recombination positive clones of ES cells by PCR analysis covering the 3' side of the recombinant insert. The larger fragment corresponds to the insertion of a neo selectable marker into the M1 exon at the position indicated in FIG. 5B.

Figure 1D:
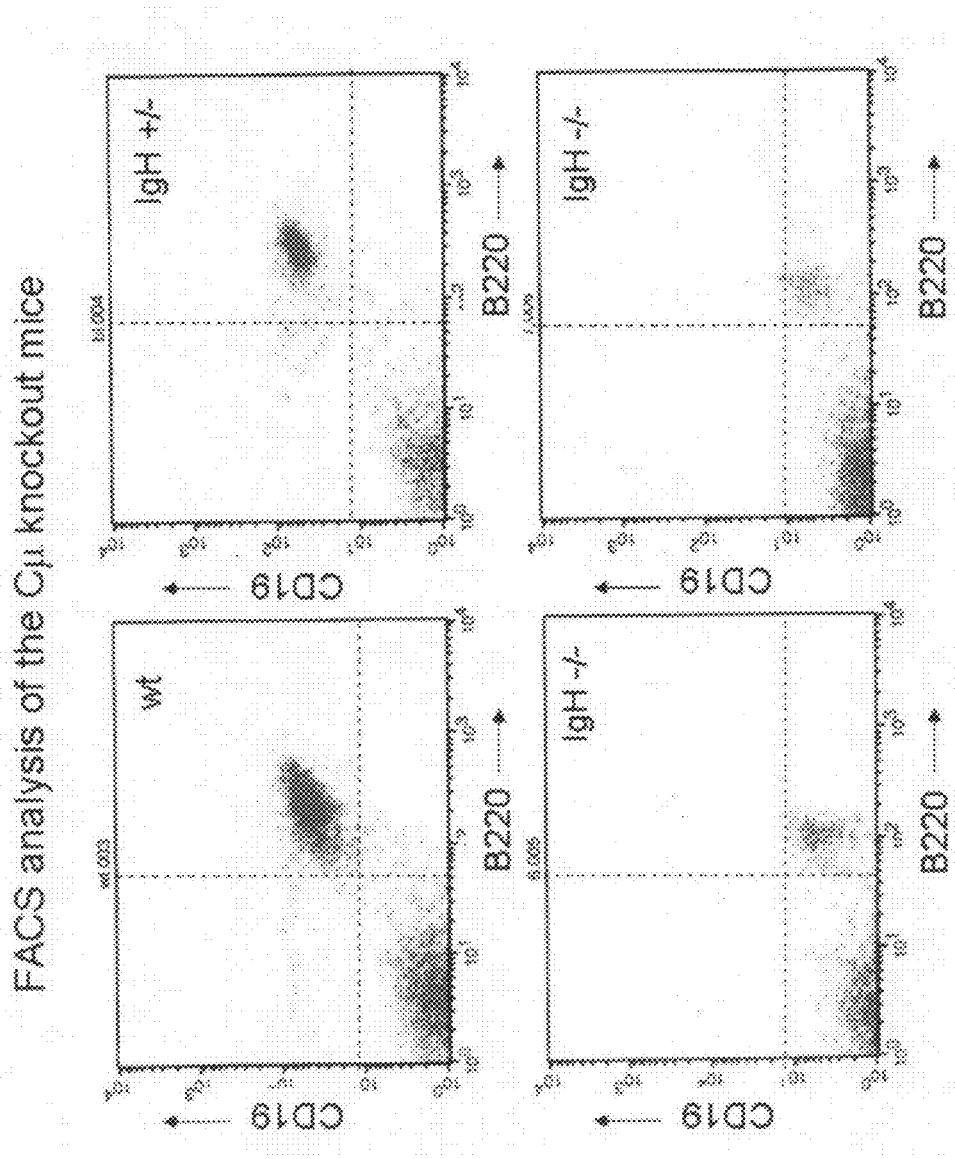

FIG. 1D: FACS Analysis of the Cμ Knockout Mice
After the M1 exon has been interrupted by the stop codon and neo gene, the ES cells are introduced into blastocysts to obtain chimeras. These are bred to homozygosity and the blood is analyzed for the presence of B cells. The top two panels show a FACS analysis of a normal wild type mouse and a heterozygous interrupted M1 exon mouse using the B cell markers B220 and CD19. The bottom two panels show two homozygous mice, which show no B220$^+$, CD19$^+$ cells, i.e. no functional B cells.

Figure 1E:
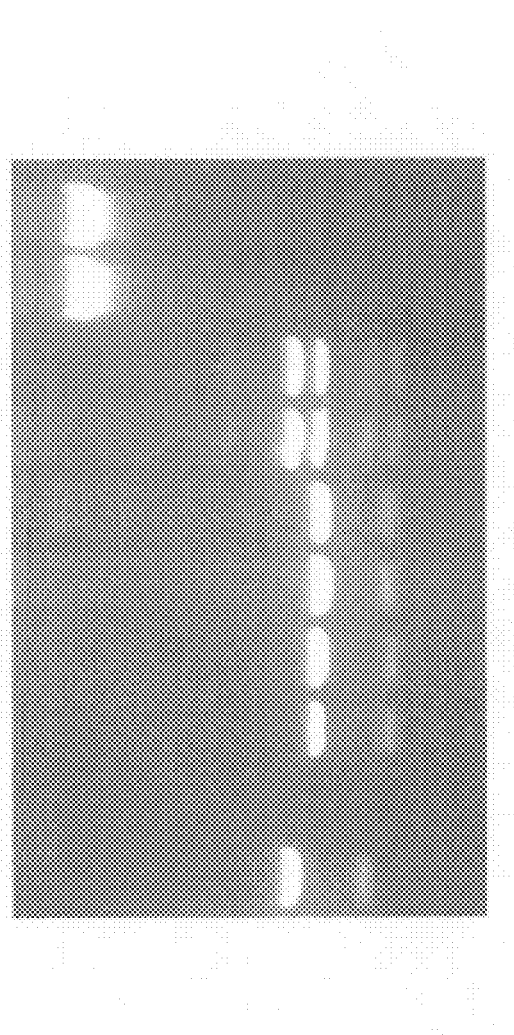

FIG. 1E: Deletion of Neo after Breeding to Recombinant Mice
The mice of FIG. 5D are crossed with recombinase-expressing mice to delete the neo gene. The two lanes on the right show a long range PCR product over the neo gene in the parent animals, the next two lanes to the left two heterozygous mice carrying a deletion of neo and a wt allele. The next four lanes lane to the left are wild type mice, while the lane furthest left show a mouse carrying a homozygous deletion of the neo gene with an inactivated M1 exon.

Figure 2:
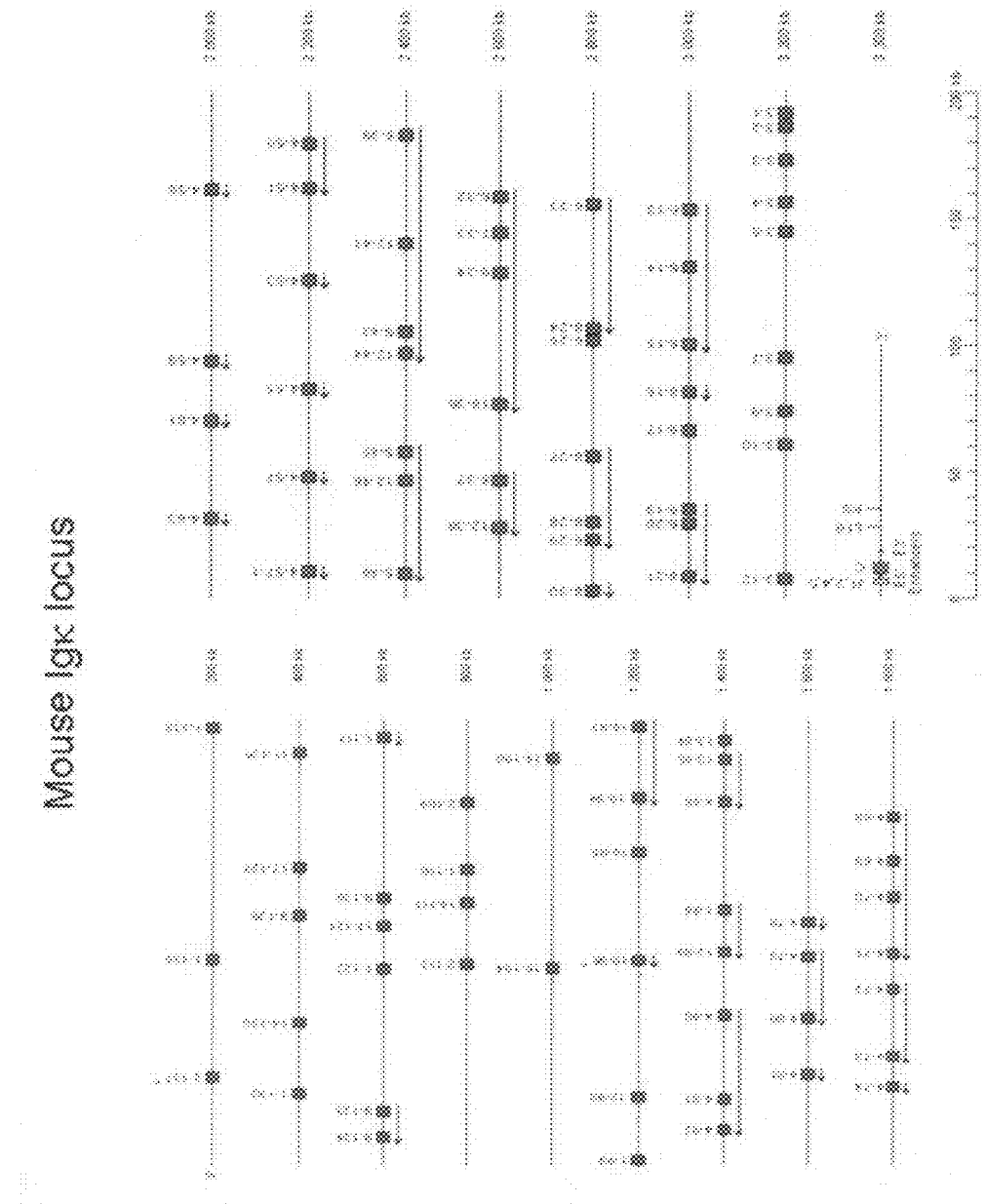

FIG. 2: A Map of the Mouse Ig$_\kappa$ Locus
The map is copied from the IMGT database (URL without the lead http reference) imgt.cines.f. The scale is in kilobases (kb). Green squares, $V_\kappa$ segments; orange squares, $J_\kappa$ segments; blue square, constant region; black circle κ-enhancer and red circle κ-LCR sequences.

Figure 3:
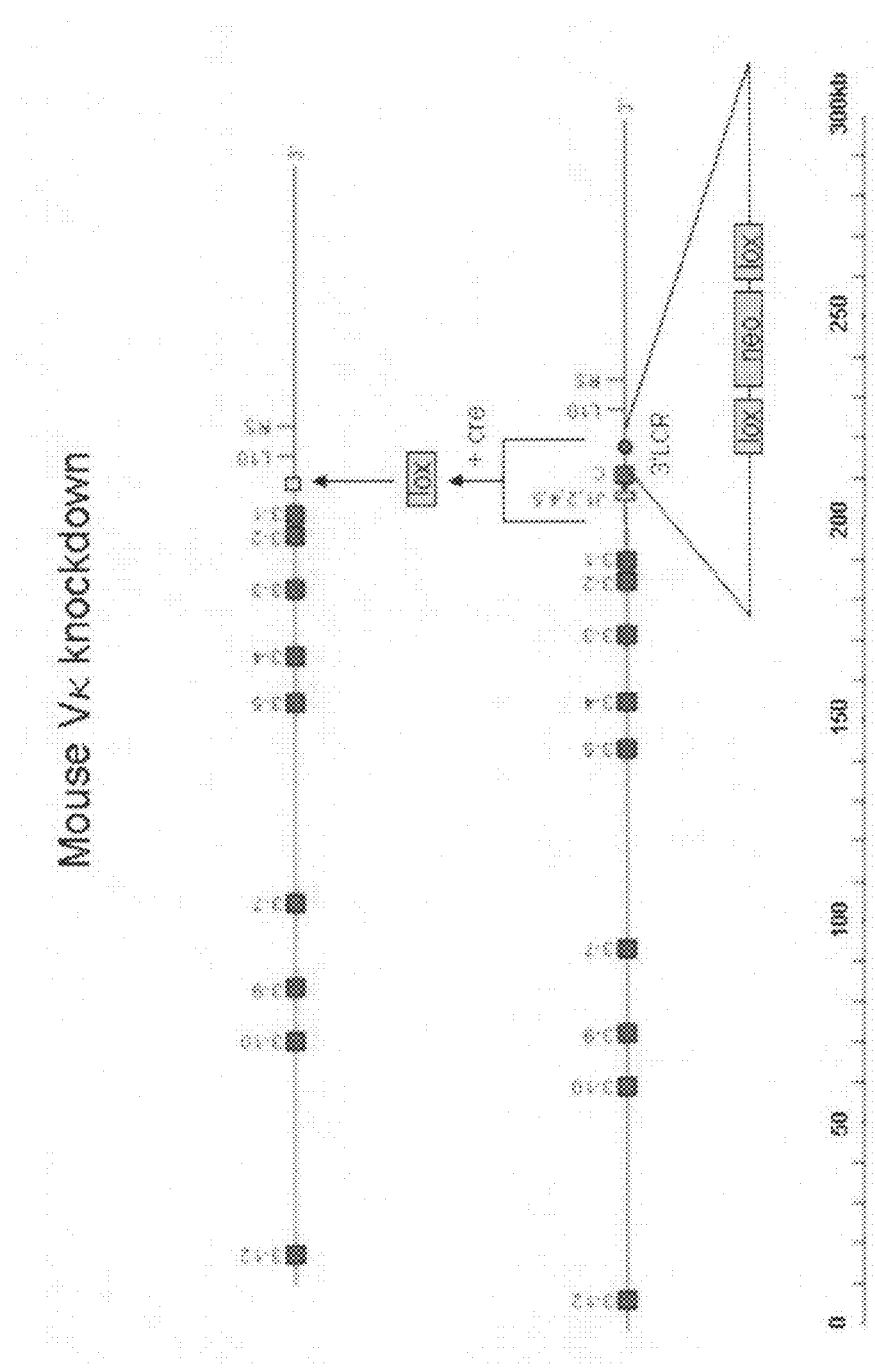

FIG. 3: Mouse $V_\kappa$ Knockdown.
Scheme to functionally inactivate the mouse Ig$_\kappa$ locus by deletion of the LCR
A lox neomycin resistance gene cassette is inserted by homologous recombination in ES cells replacing the 3'$_\kappa$-LCR (bottom line). Treatment with cre recombinase (+ cre) will remove all sequences between the lox sites, leaving a single lox site in the κ locus (top line).

Figure 4:
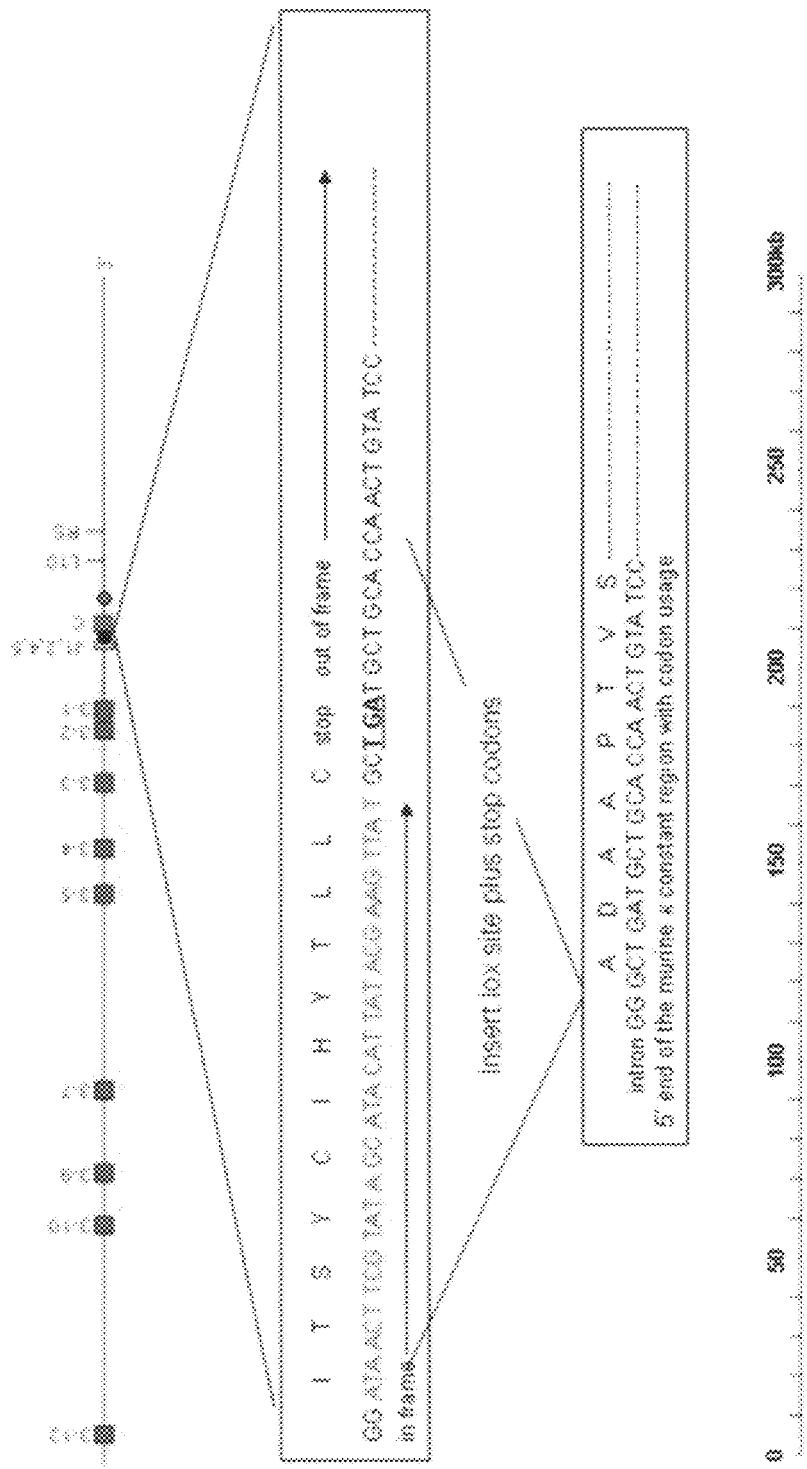

FIG. 4: A Mouse C$_\kappa$ Insertion to Inactivate the κ Locus.
The locus (top line) is the same as in FIG. 3. The bottom shows the sequence at the 5' end of the C$_\kappa$ exon (blue in top line) with the amino acid coding written above the bases. The GG base pair at the start is immediately flanking the splice acceptor site coding for the amino acid R after splicing. The middle line shows the insertion of a 34 basepair lox site insertion (blue and red inverted repeat sequence), which puts the codon usage of the constant region out of frame and creating downstream stop codons (e.g. TGA fat print underlined). Black circle κ-enhancer and red circle κ-LCR sequences.

Figure 5:
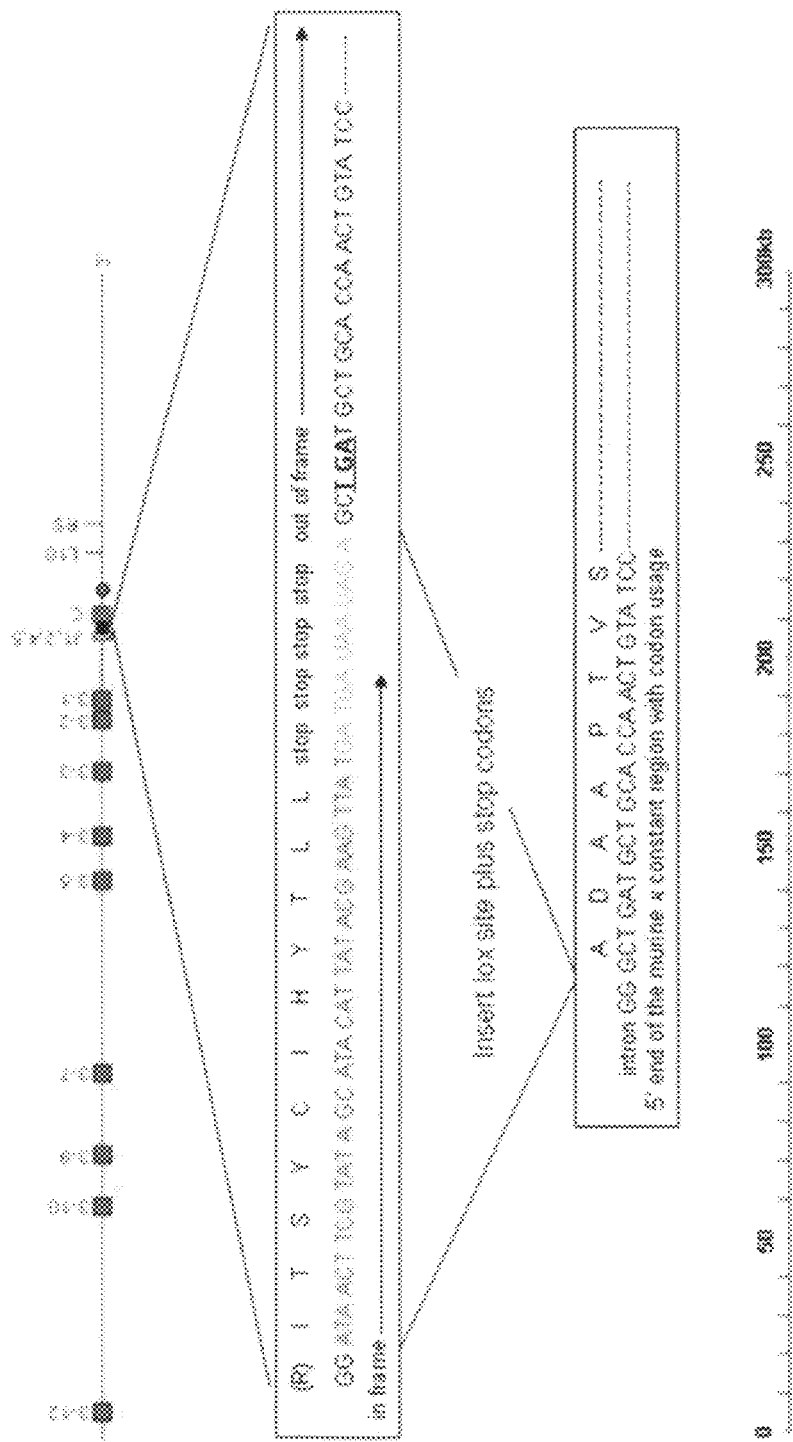

FIG. 5: A Mouse C$_\kappa$ Insertion
The locus (top line) is the same as in FIG. 3. The bottom shows the sequence at the 5' end of the C$_\kappa$ exon (blue in top line) with the amino acid coding written above the bases. The GG base pair at the start is immediately flanking the splice acceptor site coding for the amino acid R after splicing. The middle line shows the insertion of a 46 basepair insertion containing a lox sequence (blue and red inverted repeat sequence) and 4 stop codons, which also puts the codon usage of the constant region out of frame and creating downstream stop codons (e.g. TGA fat print underlined). Black circle κ-enhancer and red circle κ-LCR sequences.

Figure 6A:
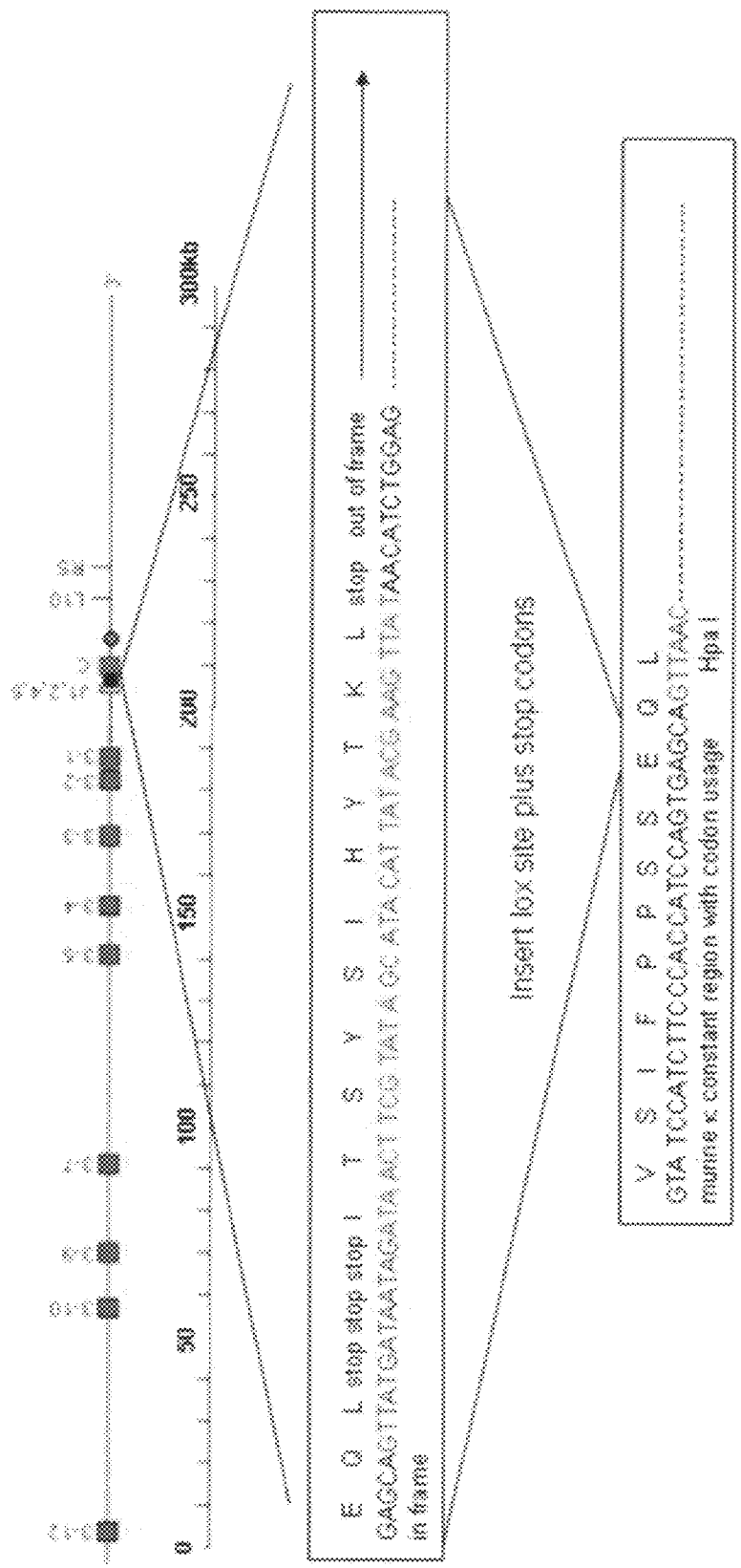

FIG. 6A: A Mouse $C_\kappa$ Constant Region Stop Codon and Frame Shift Insertion The locus (top line) is the same as in FIG. 3. The bottom shows part of the sequence of the $C_\kappa$ exon (black) with the amino acid coding written above the bases. The middle line shows part of the sequence of the $C_\kappa$ coding region. The line above it shows the insertion of a 44 basepair insertion containing a lox sequence (blue and red inverted repeat sequence), 3 stop codons, which also puts the codon usage of the constant region out of frame and creating downstream stop codons (TAA). Black circle κ-enhancer and red circle κ-LCR sequences, the Hpa I site used for the insertion is shown in red.

Figure 6B:
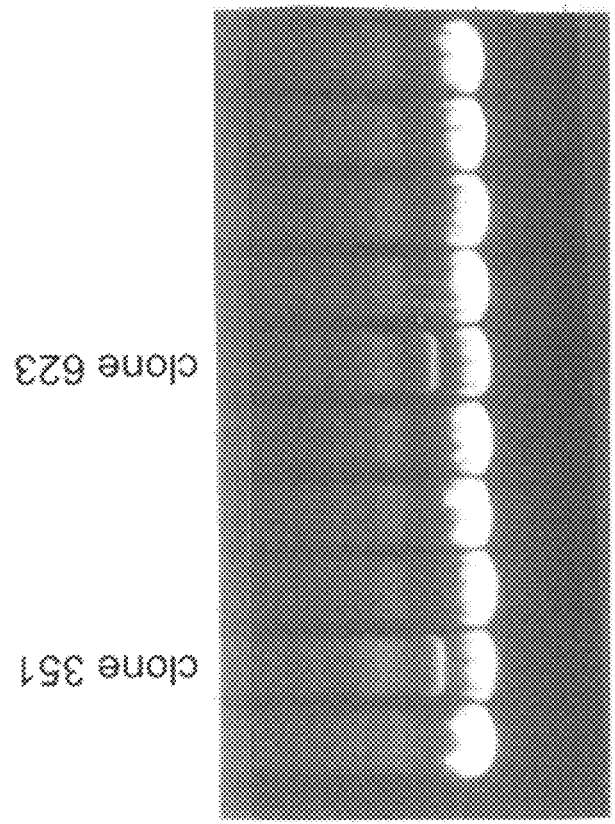

FIG. 6B: Recombination in ES Cells to Disable $C_\kappa$

Figure 13A:
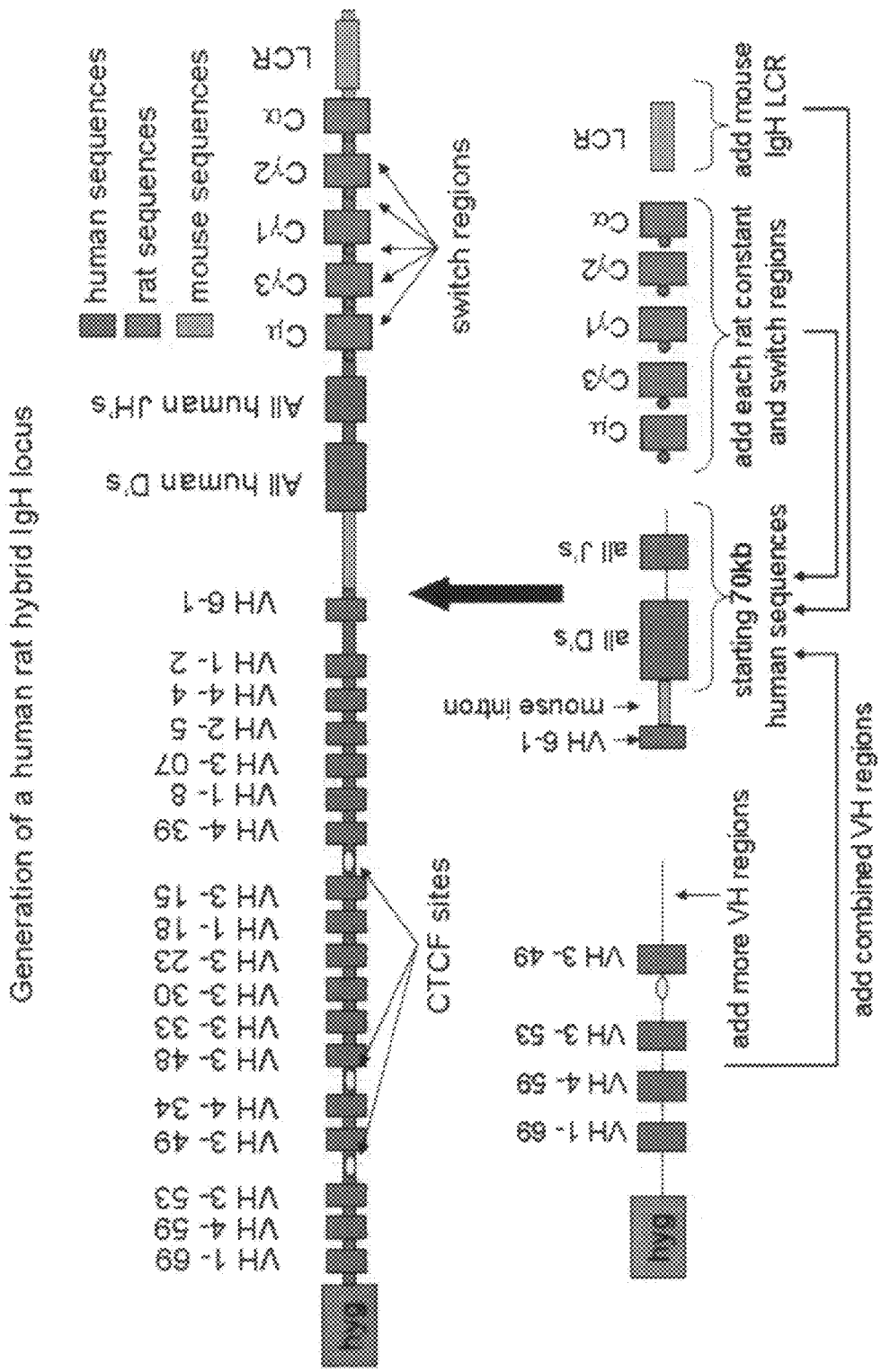

The gel shows the result of a PCR amplification over the insertion site of a number of the clones of the $C_\kappa$ recombination in ES cells illustrated in FIG. 13A. Clones 351 and 623 are positive and will be injected into blastocysts to generate $Ig_\kappa$ negative mice.

Figure 7:
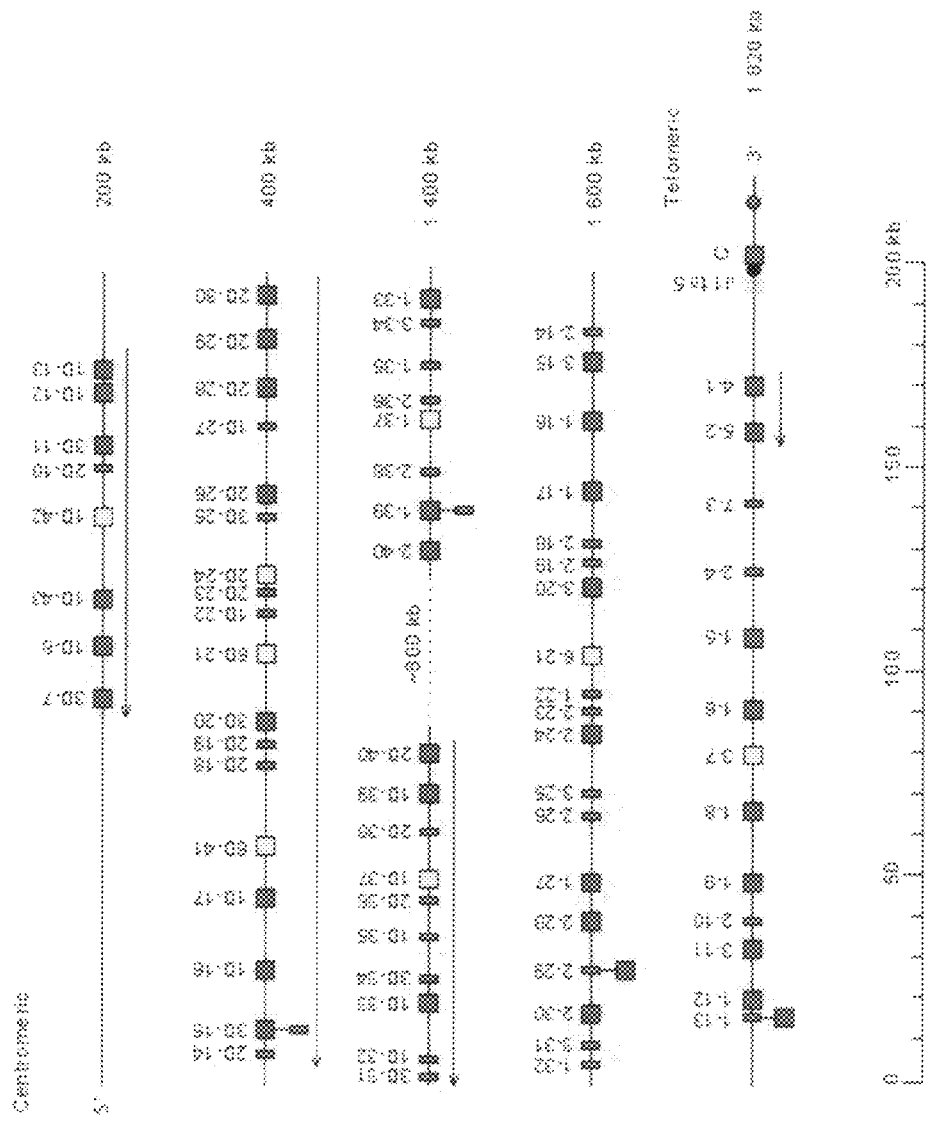

FIG. 7: The Human $Ig_\kappa$ Locus.

The map is copied from the IMGT database (URL without the lead http reference imgt.cines.f. The scale is in kilobases (kb). Green squares, functional $V_\kappa$ segments; red and yellow squares, non-functional $V_\kappa$ segments; orange squares, $J_\kappa$ segments; blue squares, constant region; black circle κ-enhancer and red circle κ-LCR sequences.

Figure 8:
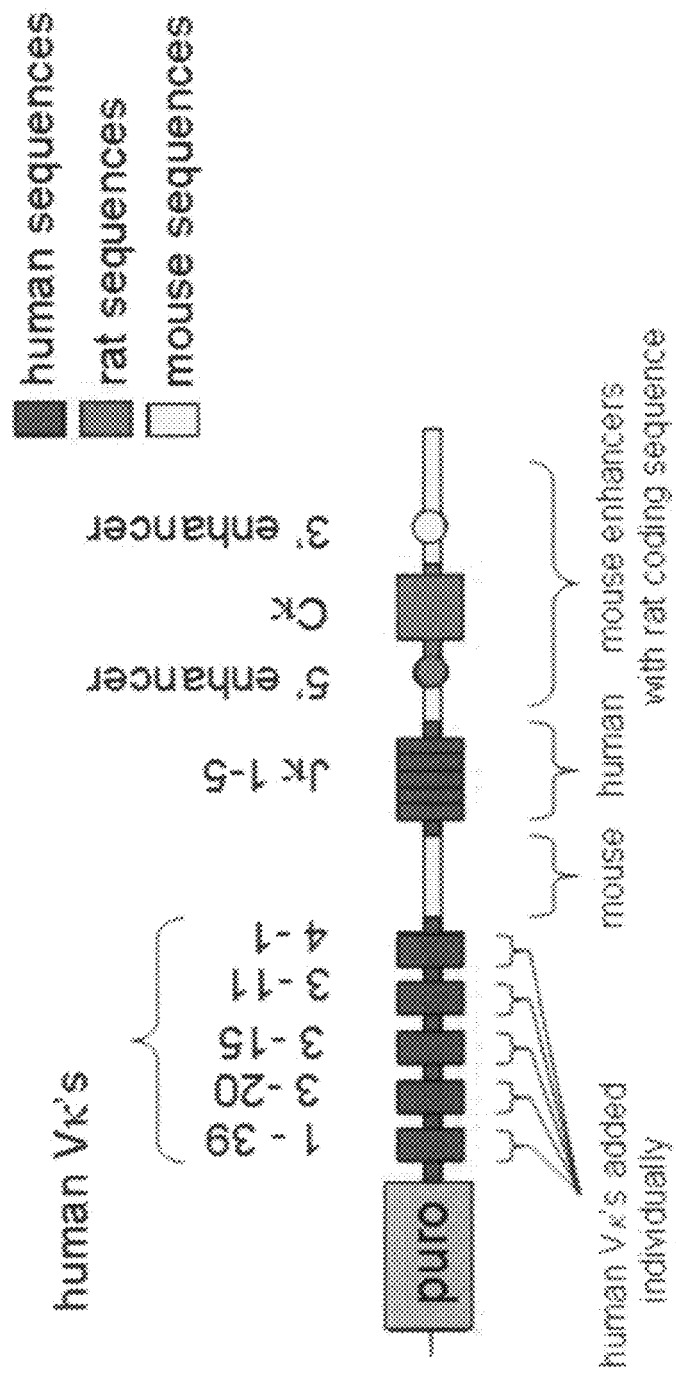

FIG. 8: Generation of a Hybrid Human/Rat $Ig_\kappa$ Locus for Transgenesis

The 3' end of the locus is obtained from the mouse (yellow) containing the mouse κ 3' enhancer (yellow). The mouse constant coding sequences are replaced with those of the rat, including its 5' enhancer obtained by long range PCR from rat genomic DNA (red). The human segment downstream from $V_\kappa 4$-1 through to the human $J_\kappa$ sequences are obtained from the mouse (yellow) to maintain the proper spacing between the V and J regions. The human $J_\kappa$ segments are obtained from a PAC covering this part of the human locus (green). The green squares are $V_\kappa$ segments added individually or as a block (see text). The puromycin resistance gene present in the PAC vector is in red, black circle κ-enhancer and red circle κ-LCR sequences.

Figure 9:
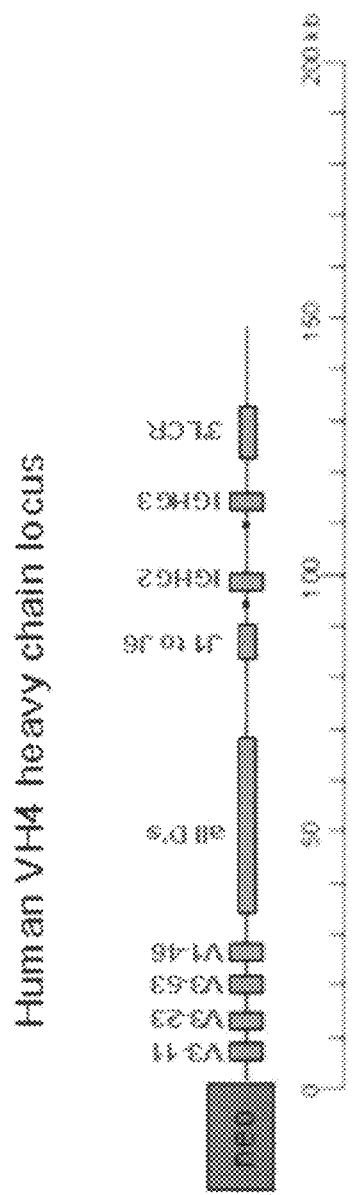

FIG. 9: A Map of the $V_H 4$ Heavy Chain Locus

This locus containing a neomycin selectable marker at the 5' end is used as the starting material for the construction of the human/mouse hybrid locus. This locus is built as described in WO2008/035216. The scale is in kilobases. The locus contains four $V_H$ regions (1-46, 3-53, 3-23, 3-11), all of the human D segments, all of the human J segments and IgG constant regions and the 3' human IgH LCR.

Figure 10:
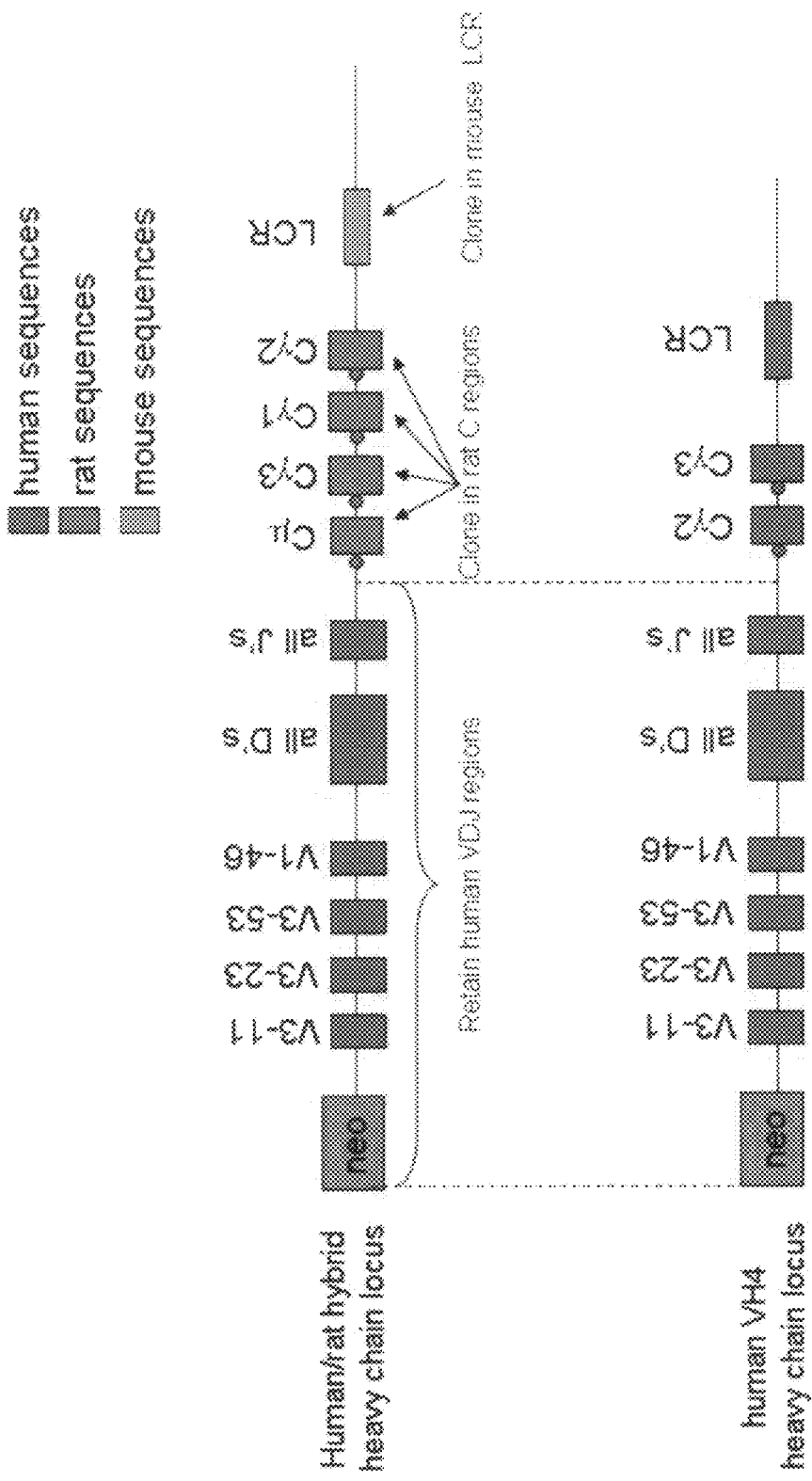

FIG. 10: Generation of a 4 $V_H$ Human/Rat Constant Region IgH Locus

A CeuI site present in the $V_H 4$ human locus (FIG. 6) is used to generate a human/rat locus by adding the rat constant coding and switch regions that have been amplified by PCR from rat genomic DNA. Similarly the mouse LCR region is amplified from mouse genomic DNA as several fragments which are first cloned together to generate the complete mouse IgH LCR. The 5' end of the human $V_H 4$ locus containing the 4 $V_H$ segments, all of the human D and all the human J segments (FIG. 6). All human sequences are in blue, all mouse sequences in light green, the rat sequences in red and the neomycin resistance gene is shown in purple.

Figure 11:
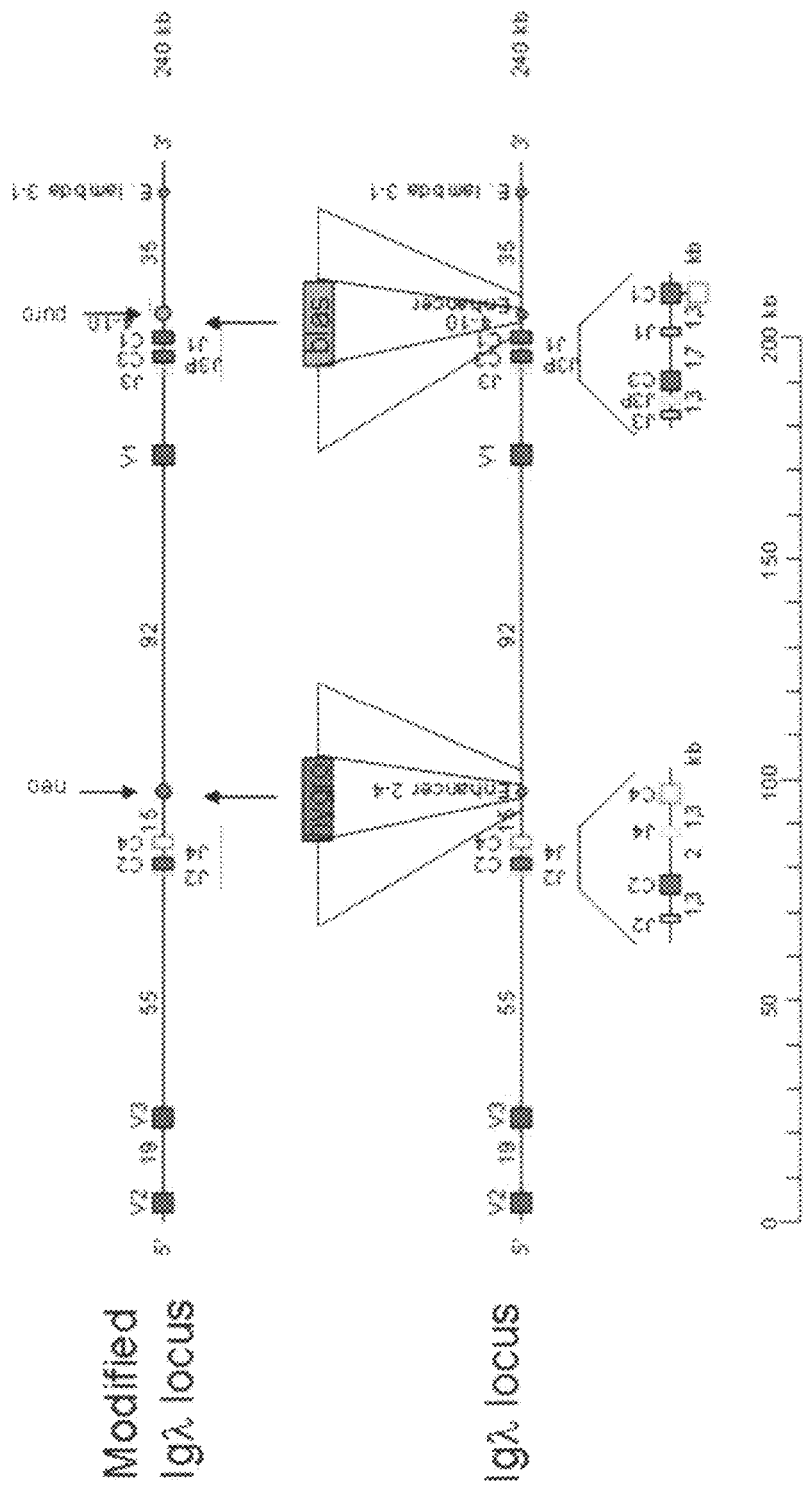

FIG. 11: Deletion of the Igλ Enhancers Comprising the λ LCR

The λ locus enhancers are removed by homologous recombination using standard replacement vectors using the hygromycin resistance gene flanked by sequences homologous to the regions flanking the enhancer 2-4 and the blasticin S resistance gene flanked by segments homologous to the regions flanking the 4-10 enhancer. Replacement results in a λ locus that has lost the enhancers and shows decreased expression. Hygromycin resistance gene is shown in red, the blasticin S resistance gene in orange. The mouse $V_\lambda$ segments are in green, the J segments in yellow and the constant regions in blue. The maps are copied from the IGMT database.

Figure 12:
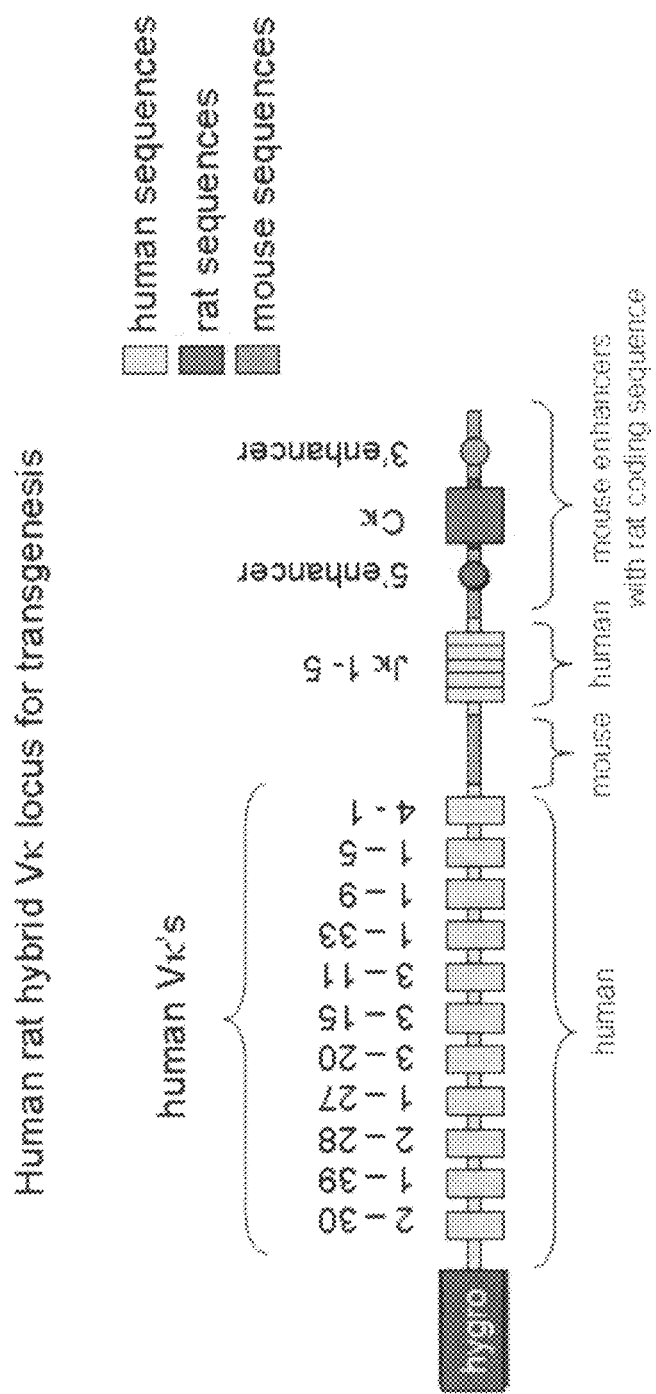

FIG. 12: A Human Rat $V_\kappa$ Locus for Transgenesis

The locus is the same as in FIG. 8, but additional human $V_\kappa$ segments have been added to the locus. The resulting locus contains all of the frequently and moderately frequently used human $V_\kappa$ segments. Green circle and green line, murine κ-enhancer and intron; red square and circle, rat κ-constant region and enhancer; blue squares, human $V_H$ segments; dark blue, puromycin selectable marker.

FIG. 13A: Generation of a Human Rat Hybrid Locus

The locus is generated by ligating $V_H$ regions together to a concatemer of 17 consecutive human $V_H$ regions cloned between SceI sites. A mouse spacer region is added to a human 40 kb fragment containing all the human $D_H$ and $J_H$ segments to keep the appropriate distance between the $D_H$ and $V_H$ segments. This is followed by the addition of a $V_H 6$-1 segment containing an SceI site. The concatemer is then added onto the $V_H 6$-1. Finally, the various rat constant regions and the murine LCR are added at the 3' side. The resulting locus contains all of the frequently and moderately frequently used human $V_H$ segments.

Figure 13B:
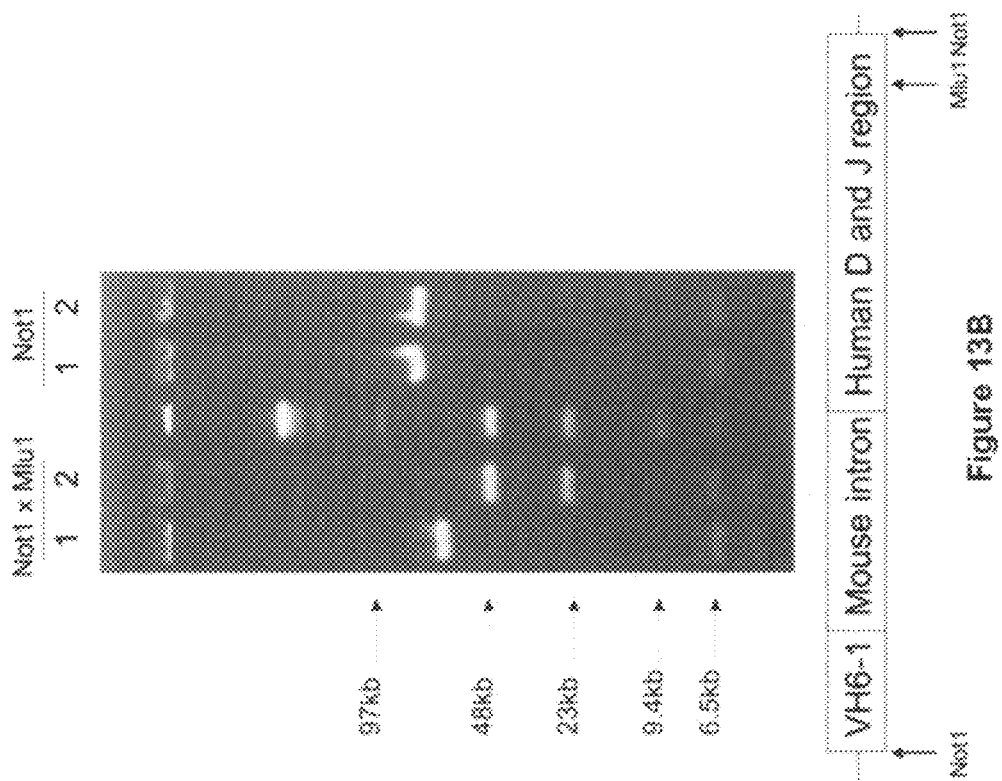

FIG. 13B: The Starting Construct of the Human/Rat IgH Locus

The gel shows the result of the first steps of the human rat IgH locus construction after the addition of $V_H 6$-1. The lanes on the right show a NotI digest of two of the cloned plasmids. The lanes (NotI×MluI) show the plasmid in lane 1 to have the correct orientation in the vector, whereas the plasmid in lane 2 has the wrong orientation. The lane 1 plasmid is used for the next step in the generation of the locus.

Figure 13C:
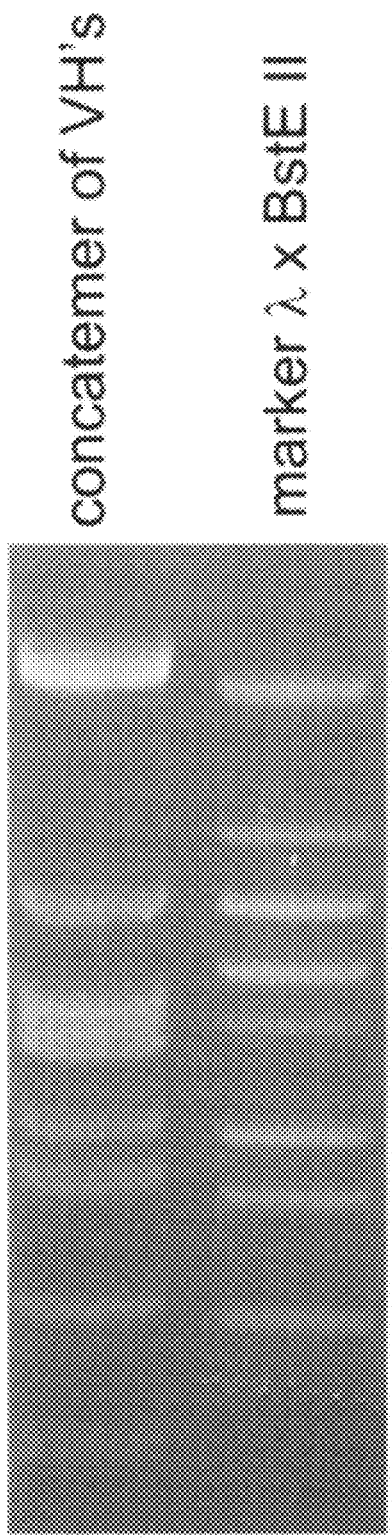

FIG. 13C: Concatemer of $V_H$ Segments

The gel shows an XhoI/SalI digest of a concatemer of 17 different $V_H$ regions. The marker lane contains a λ phage DNA digested with BstEII.

Figure 14:
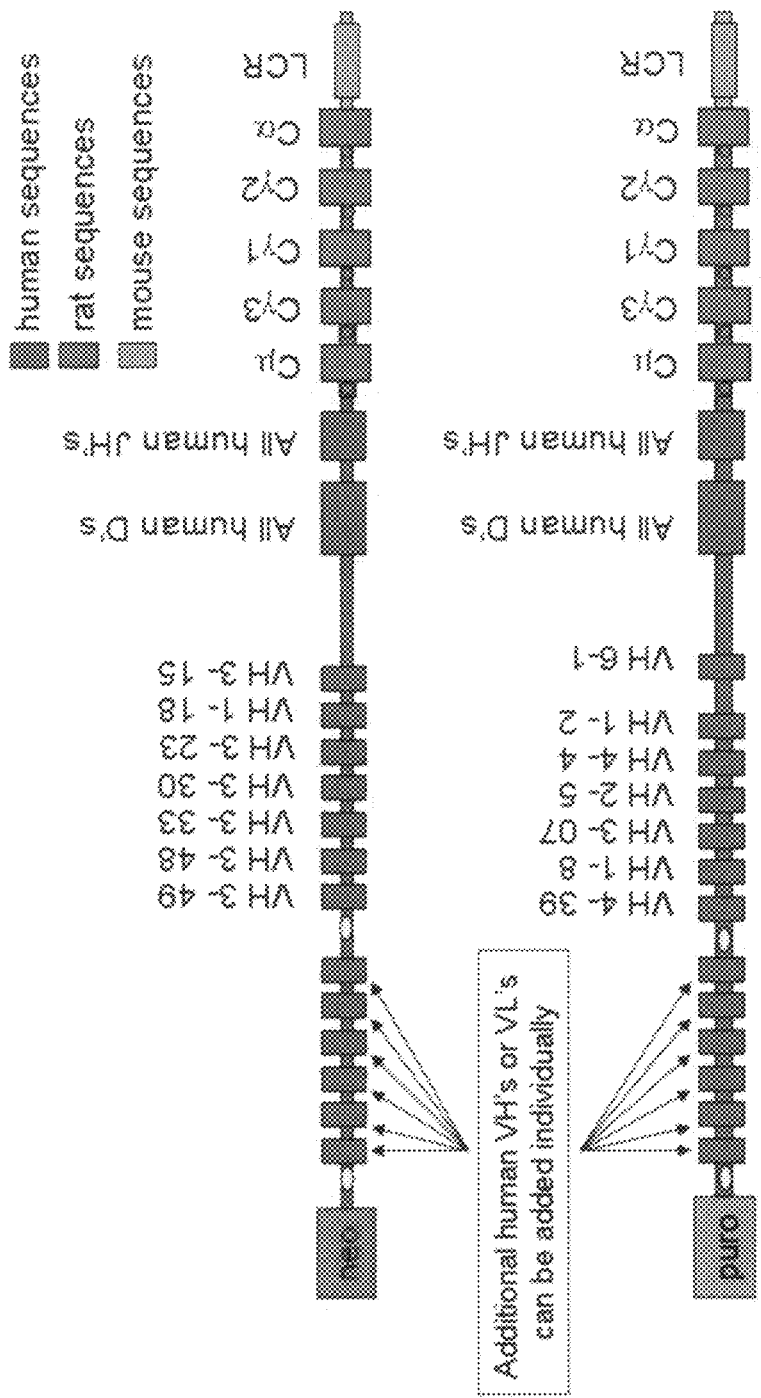

FIG. 14: Transgenic Human Rat Heavy Chain Immunoglobulin Loci.

An example of two heavy chain gene loci introduced into the same animal. Selection of one as opposed to another is through allelic exclusion. Additional $V_H$ segments could be added to each of the loci. Alternatively, additional $V_H$ segments could be introduced using further heavy chain gene loci. Obviously, the same strategy could be used to increase diversity with κ or λ light chain loci.

Figure 15:
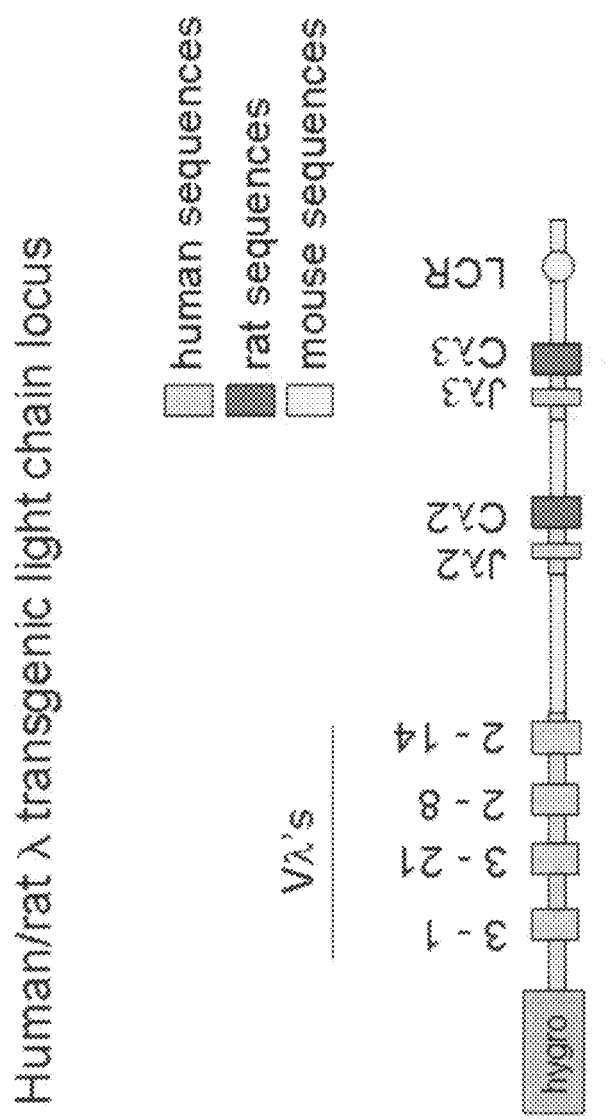

FIG. 15: Human/Rat λ Transgenic Light Chain Locus

An example of a human/rat locus is shown. Its 3' end is obtained from the mouse (yellow) containing the mouse λ 3' LCR (yellow). The mouse constant coding sequences are replaced with those of the rat by long range PCR from rat genomic DNA (red). The human segment downstream from $V_\lambda 2$-14 through to the human $J_\kappa$ sequences are obtained from the mouse (yellow) to maintain the proper spacing between the V and J regions. The human $J_\lambda$ segments are obtained by long range PCR of a human PAC covering this part of the human locus (blue). The blue squares are $V_\lambda$ segments added individually or as a block. The hygromycin resistance gene present in the PAC vector is in purple.

EXAMPLES

In the following examples, transgenic mice are generated that express hybrid human/rat heavy chain and light chain loci as transgenes introduced by microinjection in fertilised eggs, a routine transgenesis procedure. The egg-donating mice are modified to have no or very low expression of the endogenous mouse heavy chain genes and mouse light chain genes. There are two light chain loci in mice, for κ and λ chains, of which λ, is used only in approximately 2% of the mouse H2L2 antibodies.

The examples are therefore in either mice which have the IgH locus and only the endogenous κ locus inactivated or in mice which have the IgH and κ locus inactivated and the regulatory sequences of the λ locus removed to lower the expression of the λ locus even further.

Methodology used for the construction of heavy and light chain loci, the generation and screening of transgenic mice following antigen challenge are essentially as previously described (Janssens et al. (2006) PNAS, 10, 103(41), 15130-5, WO2006/008548, WO2007/096779, GB0805281.3 and the PCT application filed on 11$^{th}$ June 2008 claiming priority from GB0805281.3) excepting that the $C_H1$ domain is retained in all heavy chain loci. General methods for deriving vertebrates, including mammals, other than mice, which express functional heterologous immunoglobulin loci and/or have engineered endogenous loci are as described in WO2006/047367. In the examples below, recombination in ES cells is used and the modified ES cells are used to generate mice with the desired properties. However, the same procedures could be carried out in induced pluripotent stem cells (iPS cells) which are then used to generate mice (e.g. Boland, Hazen, Nazor, Rodriguez, Gifford, Martin, Kupriyanov and Baldwin (2009), 461, 7260, 91-4 and references therein). Alternatively, the modifications are carried out in somatic cells or somatic stem cells which are subsequently reprogrammed into iPS cells to generate modified mice. Also, modified hematopoietic stem cells could be transplanted into recipient mice lacking B cells to generate human or human hybrid antibodies.

Example 1

In this example, the IgH locus (FIG. 1A) is inactivated by a strategy similar to that published by Kitamura and Rajewsky with the difference that the stop codon is introduced into the $C^\mu$ regions at a position one amino acid before that described by Kitamura et al. (1991) Nature, 350, 423-426. ES (or iPS) cells were transfected with a construct that changes the second codon of the first membrane exon of the mouse IgM gene into a stop codon. This involves routine procedure including a neo selection for transfection. A SpeI site was included in the recombination sequences to be able to monitor the successful recombination (FIG. 1B). ES cells are subsequently screened by Southern blots to confirm successful recombinant clones. This resulted in 10 correct recombinants (e.g. FIG. 1C). Of these, 3 were injected into mouse blastocysts to obtain chimeras which were subsequently bred to obtain mice that are homozygous for the IgH mutation. FACS analysis (B220 versus CD19) of the B cells of such mice shows the absence of B cells in peripheral blood (FIG. 1D). The mice were subsequently crossed with recombinase-expressing mice to remove the neo gene (FIG. 1E). Similarly, the mouse $Ig_\kappa$ locus (FIG. 2) is inactivated or reduced by recombination in ES cells (FIG. 2, 3, 4-6). The resulting κ inactivated mice are crossed to the heavy chain KO mice. A knock down of the activity is achieved by replacing the 3' κ gene LCR with a neo resistance marker flanked by lox sites (FIG. 3). The neo gene is optionally removed by treatment with recombinase.

Alternatively, the κ alleles could be knocked out in the IgH KO cells directly. Several different strategies can be used to achieve the κ inactivation. Blocking of the activity of the κ gene can be achieved by using homologous recombination in ES cells or iPS cells to insert into the 5' end of the $C_\kappa$ exon a neo gene flanked by lox sites (FIG. 4) or by inserting a neo gene flanked by lox sites and an additional sequence coding for stop codons (FIGS. 5 and 6A). Treatment of the recombined ES cells with cre will leave the sequence out of frame (FIG. 4) or additionally contain new stop codons (FIG. 5-6A). FIG. 6B shows a recombination result in ES cells after transfection of the construct shown in FIG. 6A, resulting in two ES cells clones that have one $C)_\kappa$ allele inactivated (5 such clones were obtained in total). The cells are treated with recombinase by a standard transient transfection with an actin-driven recombinase plasmid to remove the region between the two lox sites. The cells are subsequently used to generate mice by routine methods and the progeny bred to obtain homozygous mice. Such mice comprise B-cells in which the assembly of immunoglobulin tetramers comprising kappa light chains is substantially impaired or completely blocked.

Next, the most frequently used V, genes of the human $Ig_\kappa$ locus (assessed using the Ig database; URL without the lead http reference, imgt.cines.f; see FIGS. 7, 8) are amplified by standard PCR and subcloned between XhoI/SalI sites, as described previously for human $V_H$ segments. This allows the multimerisation of the $V_\kappa$ regions, keeping the multimer between XhoI and SalI sites.

Also, the 3' end of the mouse κ locus, including the 3' κ enhancer, and the rat constant ($C_\kappa$) region plus the rat 5' enhancer are cloned together (FIG. 8). Next, the human $J_\kappa$ region and the region (17 kb) from between mouse $V_\kappa$ and $J_\kappa$ (FIG. 2) are cloned in to maintain the normal spacing between $V_\kappa$ regions and $J_\kappa$. Finally, the human $V_\kappa$ are inserted into the PAC (FIG. 8) containing a puromycin selectable marker by routine procedures (e.g. Janssens et al. (2006), supra).

In the example shown, the most frequently used $V_\kappa$ segments (4-1, 3-11, 3-15, 3-20 and 1-39) are multimerized and ligated into the PAC vector containing the human J regions and the mouse enhancers and rat $C_\kappa$, regions. This results in a human-rat hybrid locus consisting of a puro resistance marker gene, human $V_\kappa$ segments and a rat constant ($C_\kappa$) region (FIG. 8).

In parallel, a hybrid human/rat IgH locus is constructed. Again, there are a number of possibilities in terms of starting material. In this example, the starting material is a human PAC containing 4 human $V_H$ regions, all of the human $D_H$ and $J_H$ segments and two human constant regions and the human LCR (FIG. 9 and UK patent application No 0905023.8).

The latter PAC has a unique CeuI meganuclease site in between the J regions and the constant regions. To allow easy construction of the hybrid locus, this CeuI site is used to remove the human 3' end sequence and replace these with rat constant and switch regions (Cμ, Cγ3, Cγ1 and Cγ2). These have been amplified by standard long range PCR from rat genomic DNA. Finally, the mouse heavy chain LCR is added. This regulatory sequence is amplified from mouse genomic DNA in three parts, subcloned together to restore the complete LCR and added to the 3' side of the rat constant regions (FIG. 10). The resulting hybrid IgH locus thus contains a neo selection marker, human V, D and J regions and rat constant regions with mouse regulatory sequences.

The hybrid loci inserts are subsequently isolated from the PAC as large DNA fragments and injected into fertilized mouse eggs derived from the IgH/Ig$_\kappa$ heterozygous or homozygous null mice to generate mice that are transgenic for the human/rat hybrid IgH and Ig$_\kappa$ loci. All of this is done by routine methods (e.g. Janssens et al. (2006), supra).

The hybrid IgH and hybrid Ig$_\kappa$ transgenic mice are subsequently bred to obtain mice that are homozygous null for the endogenous mouse IgH and Ig), expression and positive for the human/rat hybrid IgH and Ig$_\kappa$ expression. These mice are subsequently immunized to generate antigen-specific hybrid human/rat H$_2$L$_2$ antibodies by routine procedures. When generating monoclonal human/rat Igs through hybridomas, double selection in puromycin and neomycin will ensure that only myeloma fusions containing both an IgH and an Ig$_\kappa$ locus will selected for.

The skilled person will appreciate that variations to this procedure may be made to generate the hybrid transgenic mice, such as the use of different vectors, different selection markers, different recombination positions to inactivate the mouse genes or variations in the actual (routine) cloning strategy of the hybrid loci. The same procedure can be used to generate any normal or hybrid locus using immunoglobulin DNA derived from any single mammalian species, or hybrid loci derived using DNA from two or more species.

Example 2

This example is in principle the same as Example 1 with the exception that the high frequency of obtaining IgH/Ig$_\kappa$ H$_2$L$_2$ antibodies is increased even further by lowering the frequency of expression of the endogenous mouse Ig$_\lambda$ locus. This can be achieved by replacing the regulatory regions of both Ig$_\lambda$ with a selectable marker (FIG. 11), in this case the hygromycin resistance gene and the TK-BSD gene.

The latter allows positive selection, resistance to blasticidin S (Karreman, (1998) NAR, 26, (10), 2508-2510). This combination of markers allows for positive selection in the two ES cell recombinations when replacing the regulatory regions. The recombination would be carried out in the ES cells generated in Example 1 or alternatively in parallel in normal ES cells and bred into the mice described above in Example 1.

The resulting transgenic mice would contain the hybrid human rat IgH and Ig$_\kappa$ loci, be negative for endogenous mouse IgH and Ig$_\kappa$ (or express C$_\kappa$ at very low levels) and express Ig$_x$ at very low levels. After immunization and the generation of hybridomas by routine methods, the hybridomas expressing only human rat hybrid H2L2 antibodies would be selected for expression of the transgenic hybrid loci by neo (FIG. 10) and puro (FIG. 8) selection.

Example 3

Example 3 is analogous to the Examples described above but the hybrid Ig$_\kappa$ locus would be extended by the addition of V$_\kappa$ segments that are used less frequently (FIG. 12; V$_\kappa$ 1-9, 1-33, 2-30, 2-28, 1-27, 1-5). Alternatively, mutated/modified V$_\kappa$ segments or V$_\lambda$ segments could be added in addition. The addition of further segements would be carried out by using the same XhoI/SalI cloning strategy described above. Immunization of mice generated in this example would allow a greater complexity in response to the immunization with antigen. The number of V$_L$ regions could be varied further by adding other V$_\kappa$ segments or the use of combinations of all of the above V$_L$ segments.

Example 4

Example 4 is analogous to that described in the examples described above, but here the hybrid human/rat IgH locus has been generated by using 18 V$_H$ segments and 5 rat constant regions (FIG. 13A; human V$_H$ 6-1, 1-2, 4-4, 2-5, 3-07, 1-8, 4-39, 3-15, 1-18, 3-23, 3-30, 3-33, 3-48, 4-34, 3-49, 3-53, 4-59, 1-69). First a central 70 kb DJ region of the human locus is extended at the 5' end with 8 kb from the mouse IgH intron to maintain the proper distance between V$_H$ segments and the D region. Next the first V$_H$ region (6-1) of 10 kb with an artificial SceI meganuclease site is cloned at the 5' end of the mouse intron sequences (FIG. 10B). In a separate plasmid, all the remaining V$_H$ region are cloned together by slotting in XhoI/SalI V$_H$ segments as described above (FIG. 10C). One could also add to these loci more V$_H$ segments or V$_H$ segments that have been modified/mutated. One can also include CTCF sites. In the example shown, three such sites have been used. They are obtained by long range PCR of the V$_H$ region including the upstream CTCF site. Furthermore, the rat C$_a$ has been added when compared to the locus in FIG. 10. In this Example, immunization would allow an even greater complexity in response to the immunization with antigen, particularly in combination with Example 3. The V$_H$ multimer is cloned into the VH6-1DJ plasmid, after which the rat constant regions are added to complete the locus.

In all of these Examples, the complexity of the response will be enhanced even further by adding V segments as part of additional heavy or light chain transgenic loci present in the same mouse. Since all the loci are subject to allelic exclusion (see WO2007/096779), only the preferred rearrangement will be selected in vivo following antigen challenge, resulting in B-cell expansion and the accumulation of antibody in serum. FIG. 14 shows an example of two heavy chain gene loci that can be introduced into the same animal and each will be used through allelic exclusion. Obviously, more V$_H$ segments could be added (including modified V$_H$ segments) or even more loci could be introduced to increase the complexity of the transgenic immune repertoire. The method could also be applied to other species using V segments specific for these species.

Example 5

In this example, the diversity of the human/rat hybrid antibody is increased even further by the addition of a human/rat Igλ locus through breeding to the mice that carry human/rat IgH and/or Igκ loci described in the examples above. The human/rat hybrid λ locus is generated very much as described for the human/rat Igκ locus described in the previous examples. The difference is caused by the fact that Jλ and Cλ regions occur in pairs and hence 2 rat C$_\lambda$ regions are, cloned onto 2 human J$_\lambda$ regions (FIG. 15). The spacing between the V$_\lambda$ and J$_\lambda$ segments is maintained by cloning the normal mouse sequences that occur in that position (see FIG. 11). In this example, 2 human J$_\lambda$ and rat C$_\lambda$ segments are used together with four human V$_\lambda$ segments. Together, these cover more than 80% of the human Igλ response. The regulatory sequences (LCR, FIG. 15) are derived from the mouse to ensure optimal expression, and a selectable marker is added at the 5' end of the locus. As described above, the locus is isolated as a restriction fragment and injected into fertilised eggs to generate mice carrying the transgenic λ locus.

In all of these examples V$_H$, V$_L$, D, J and constant regions from different species can be used to generate other single species antibodies or hybrid species antibodies. It will also be apparent to one skilled in the art that, once an antigen-specific antibody has been identified, the V$_H$DJ and V$_L$J regions regions can be cloned onto alternative constant regions from the same species or from different species by completely routine methods.

We claim:
1. A transgenic non-human mammal comprising a heterologous immunoglobulin heavy chain locus comprising human VH gene segments, one or more human D gene segments, human J gene segments, and rat constant region gene segments, wherein the human VH gene segments consist of VH1-69, VH4-59, VH3-53, VH3-49, VH4-34, VH3-48, VH3-33, VH3-30, VH3-23, VH1-18, VH3-15, VH4-39, VH1-8, VH3-07, VH2-5, VH4-4, VH1-2, and VH6-1, the human J gene segments comprise all six human J gene segments, and the rat constant region gene segments comprise at least Cμ and a Cγ and wherein said transgenic non-human mammal is capable of expressing a heavy chain from said heterologous heavy chain locus in response to antigen challenge, leading to the circulation of antigen-specific affinity matured, tetrameric immunoglobulins in the transgenic non-human mammal serum.

2. A transgenic non-human mammal comprising a heterologous immunoglobulin kappa light chain locus comprising human Vκ gene segments, human J gene segments, and a rat constant region gene segment, wherein the human Vκ gene segments consist of Vκ2-30, Vκ1-39, Vκ2-28, Vκ1-27, Vκ3-20, Vκ3-15, Vκ3-11, Vκ1-33, Vκ1-9, Vκ1-5, and Vκ4-1, the human J gene segments comprise all five human Jκ gene segments, and the rat constant region gene segment comprises Cκ and wherein said transgenic non-human mammal is capable of expressing a kappa light chain from said heterologous immunoglobulin kappa light chain locus in response to antigen challenge, leading to the circulation of antigen-specific affinity matured, tetrameric immunoglobulins in the transgenic non-human mammal serum.

3. A transgenic non-human mammal comprising a heterologous immunoglobulin lambda light chain locus comprising human Vλ gene segments, two human Jλ gene segments, and two rat constant region gene segments, wherein the human Vλ gene segments consist of Vλ3-1 and Vλ2-8, and the rat constant region gene segments comprise Cλ2 and Cλ3 and wherein said transgenic non-human mammal is capable of expressing a lambda light chain from said heterologous immunoglobulin lambda light chain locus in response to antigen challenge, leading to the circulation of antigen-specific affinity matured, tetrameric immunoglobulins in the transgenic non-human mammal serum.

4. The transgenic non-human mammal of claim 1, further comprising a heterologous immunoglobulin kappa light chain locus comprising human Vκ gene segments, human J gene segments, and a rat constant region gene segment, wherein the human Vκ gene segments consist of Vκ2-30, Vκ1-39, Vκ2-28, Vκ1-27, Vκ3-20, Vκ3-15, Vκ3-11, Vκ1-33, Vκ1-9, Vκ1-5, and Vκ4-1, the human J gene segments comprise all five human Jκ gene segments, and the rat constant region gene segment comprises Cκ and wherein said transgenic non-human mammal is capable of expressing a kappa light chain from said heterologous immunoglobulin kappa light chain locus in response to antigen challenge, leading to the circulation of antigen-specific affinity matured, tetrameric immunoglobulins in the transgenic non-human mammal serum.

5. The transgenic non-human mammal of claim 4, further comprising a heterologous immunoglobulin lambda light chain locus comprising at least two Vλ gene segments, two human Jλ gene segments, and two rat constant region gene segments, wherein the human Vλ gene segments comprise at least Vλ3-1 and Vλ2-8, and the rat constant region gene segments comprise Cλ2 and Cλ3 and wherein said transgenic non-human mammal is capable of expressing a lambda light chain from said heterologous immunoglobulin lambda light chain locus in response to antigen challenge, leading to the circulation of antigen-specific affinity matured, tetrameric immunoglobulins in the transgenic non-human mammal serum.

6. The transgenic non-human mammal of claim 1, further comprising a heterologous immunoglobulin lambda light chain locus comprising at least two human Vλ gene segments, two human Jλ gene segments, and two rat constant region gene segments, wherein the human Vλ gene segments comprise at least Vλ3-1 and Vλ2-8, and the rat constant region gene segments comprise Cλ2 and Cλ3 and wherein said transgenic non-human mammal is capable of expressing a lambda light chain from said heterologous immunoglobulin lambda light chain locus in response to antigen challenge, leading to the circulation of antigen-specific affinity matured, tetrameric immunoglobulins in the transgenic non-human mammal serum.

7. The transgenic non-human mammal according to any one of claims 1 to 6, wherein said locus or loci further comprise a selectable marker.

8. The transgenic non-human mammal according to claim 7, wherein more than one transgene is present, and each transgene comprises a different selectable marker.

9. The transgenic non-human mammal according to any one of claims 1 to 6, wherein the mammal is a rodent.

10. The transgenic non-human mammal according to claim 9, wherein the rodent is a mouse.

11. A method of producing an antigen-specific heterologous hybrid monoclonal antibody comprising:
(a) immunising a non-human transgenic mammal of any one of claims 4 to 6 with the antigen;
(b) preparing hybridomas or immortalised B-cell lines each of which produces a monoclonal antibody from the B-cells of the immunised transgenic mammal;
(c) optionally selecting at least one hybridoma or immortalised B-cell line expressing the heterologous antibody by use of the dominant selective marker genes present in the transgenes comprising the heterologous immunoglobulin light chain and heavy chain loci; and
(d) selecting at least one hybridoma or immortalised B-cell line which produces an antibody which binds specifically to the antigen.

12. A method of deriving a human, antibody from a hybrid antibody comprising:
(a) carrying out the method of claim 11;
(b) selecting at least one hybridoma or immortalised B-cell line which produces an antibody which binds specifically to the antigen and comprises $V_H$ and $V_L$ binding domains of the species of choice;
(c) cloning and sequencing the $V_H$ and $V_L$ domains;
(d) recloning selected sequences comprising the $V_H$ and $V_L$ binding domain coding sequences with constant effectors domains of choice from the same species; and
(e) co-expressing the recloned sequences encoding heavy and light chain polypeptides of the desired species using an expression vector in a cell type of choice.

* * * * *